United States Patent
Tian et al.

(10) Patent No.: US 11,984,225 B2
(45) Date of Patent: May 14, 2024

(54) MEDICAL IMAGE PROCESSING METHOD AND APPARATUS, ELECTRONIC MEDICAL DEVICE, AND STORAGE MEDIUM

(71) Applicant: TENCENT TECHNOLOGY (SHENZHEN) COMPANY LIMITED, Shenzhen (CN)

(72) Inventors: Kuan Tian, Shenzhen (CN); Cheng Jiang, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 390 days.

(21) Appl. No.: 17/367,280

(22) Filed: Jul. 2, 2021

(65) Prior Publication Data
US 2021/0343016 A1 Nov. 4, 2021

Related U.S. Application Data

(63) Continuation of application No. PCT/CN2020/084147, filed on Apr. 10, 2020.

(30) Foreign Application Priority Data

May 22, 2019 (CN) .......................... 201910429414.9

(51) Int. Cl.
*G06T 7/62* (2017.01)
*G06F 18/213* (2023.01)
(Continued)

(52) U.S. Cl.
CPC ........... *G16H 50/20* (2018.01); *G06F 18/213* (2023.01); *G06F 18/22* (2023.01); *G06N 20/00* (2019.01);
(Continued)

(58) Field of Classification Search
CPC . G06T 7/0014; G06T 7/11; G06T 7/62; G06T 2207/20021; G06T 2207/30096;
(Continued)

(56) References Cited

U.S. PATENT DOCUMENTS 10,789,288 B1 * 9/2020 Ranzinger ................. G06T 7/70
10,885,386 B1 * 1/2021 Evans ..................... G06V 10/44
(Continued)

FOREIGN PATENT DOCUMENTS

CN 101727537 A 6/2010
CN 103815926 A 5/2014
(Continued)

OTHER PUBLICATIONS

The World Intellectual Property Organization (WIPO) International Search Report for PCT/CN2020/084147 dated Jul. 14, 2020 8 Pages (including translation).
(Continued)

*Primary Examiner* — Ming Y Hon
(74) *Attorney, Agent, or Firm* — ANOVA LAW GROUP, PLLC

(57) ABSTRACT

A medical image processing method includes: obtaining a biological tissue image including a biological tissue, recognizing, in the biological tissue image, a first region of a lesion object in the biological tissue; recognizing a lesion attribute matching the lesion object; dividing an image region of the biological tissue in the biological tissue image into a plurality of quadrant regions; obtaining target quadrant position information of a quadrant region in which the first region is located; and generating medical service data according to the target quadrant position information and the lesion attribute.

18 Claims, 10 Drawing Sheets

(51) Int. Cl.

| | | |
|---|---|---|
| *G06F 18/22* | (2023.01) | |
| *G06N 20/00* | (2019.01) | |
| *G06T 7/00* | (2017.01) | |
| *G06T 7/11* | (2017.01) | |
| *G06V 10/10* | (2022.01) | |
| *G06V 10/25* | (2022.01) | |
| *G06V 10/26* | (2022.01) | |
| *G06V 10/82* | (2022.01) | |
| *G06V 30/19* | (2022.01) | |
| *G06V 30/262* | (2022.01) | |
| *G16H 30/20* | (2018.01) | |
| *G16H 30/40* | (2018.01) | |
| *G16H 50/20* | (2018.01) | |
| *G16H 50/70* | (2018.01) | |

(52) U.S. Cl.
CPC .............. *G06T 7/0014* (2013.01); *G06T 7/11* (2017.01); *G06T 7/62* (2017.01); *G06V 10/17* (2022.01); *G06V 10/25* (2022.01); *G06V 10/26* (2022.01); *G06V 10/82* (2022.01); *G06V 30/19147* (2022.01); *G06V 30/19153* (2022.01); *G06V 30/19173* (2022.01); *G06V 30/274* (2022.01); *G16H 30/20* (2018.01); *G16H 30/40* (2018.01); *G16H 50/70* (2018.01); *G06T 2207/20021* (2013.01); *G06T 2207/30096* (2013.01); *G06V 2201/03* (2022.01)

(58) Field of Classification Search
CPC ........ G06V 10/17; G06V 10/25; G06V 10/26; G06V 10/82; G06V 30/19147; G06V 30/19153; G06V 30/19173; G06V 30/274; G06V 2201/03
See application file for complete search history.

(56) References Cited

U.S. PATENT DOCUMENTS

| | | | | |
|---|---|---|---|---|
| 11,763,558 | B1* | 9/2023 | Casaburo | G06V 20/20 382/154 |
| 2011/0123087 | A1* | 5/2011 | Nie | G06T 7/62 345/629 |
| 2012/0014578 | A1 | 1/2012 | Karssemeijer et al. | |
| 2016/0338660 | A1 | 11/2016 | Erhard | |
| 2017/0053403 | A1 | 2/2017 | Fieselmann | |
| 2017/0221201 | A1 | 8/2017 | Chang et al. | |
| 2019/0050648 | A1* | 2/2019 | Stojanovic | G06V 20/13 |
| 2019/0108396 | A1* | 4/2019 | Dal Mutto | G06F 18/24 |
| 2020/0303062 | A1 | 9/2020 | Tao | |
| 2020/0327671 | A1* | 10/2020 | Arbel | G06T 7/11 |
| 2021/0035304 | A1* | 2/2021 | Jie | G06V 10/25 |
| 2021/0042564 | A1 | 2/2021 | Xiao et al. | |
| 2022/0284701 | A1* | 9/2022 | Cantero Clares | G06V 20/64 |

FOREIGN PATENT DOCUMENTS

| | | |
|---|---|---|
| CN | 105979875 A | 9/2016 |
| CN | 106339591 A | 1/2017 |
| CN | 107067402 A | 8/2017 |
| CN | 108427951 A | 8/2018 |
| CN | 108682015 A | 10/2018 |
| CN | 109002846 A | 12/2018 |
| CN | 109447966 A | 3/2019 |
| CN | 109461495 A | 3/2019 |
| CN | 109493343 A | 3/2019 |
| CN | 109583440 A | 4/2019 |
| CN | 109949271 A | 6/2019 |
| CN | 110033456 A | 7/2019 |
| CN | 110136809 A | 8/2019 |
| WO | 2018120942 A1 | 7/2018 |

OTHER PUBLICATIONS

The State Intellectual Property Office of the People's Republic of China (SIPO) Office Action 1 for for 201910718873.9, dated Sep. 7, 2020 16 Pages (including translation).

The State Intellectual Property Office of the People's Republic of China (SIPO) Office Action 3 for for 201910718873.9, dated Jan. 13, 2021 18 Pages (including translation).

Yuefeng Jiang, "(Non-official translation) Research on Computer Aided Diagnosis for Mammography," Chinese Master's Theses Full-Text Database, Medicine & Health Sciences, No. 01, Jun. 15, 2002 (Jun. 15, 2002), section 5.1.5. 6 pages.

Weidong Xu, "(Non-official translation) Research on Computer Aided Diagnosis Technology of Mammography," Full-text Database of China's Excellent Doctoral Dissertations, Sep. 15, 2006 (Sep. 15, 2006), section 2.3. 37 pages.

The European Patent Office (EPO) Extended Search Report for EP Application No. 20809816.0 dated Sep. 20, 2022 14 Pages.

* cited by examiner

MEDICAL IMAGE PROCESSING METHOD AND APPARATUS, ELECTRONIC MEDICAL DEVICE, AND STORAGE MEDIUM

CROSS-REFERENCES TO RELATED APPLICATIONS

This application is a continuation application of PCT Patent Application No. PCT/CN2020/084147, entitled "MEDICAL IMAGE PROCESSING METHOD AND APPARATUS, ELECTRONIC MEDICAL DEVICE, AND STORAGE MEDIUM" and filed on Apr. 10, 2020, which claims priority to Chinese Patent Application No. 201910429414.9, entitled "MEDICAL IMAGE PROCESSING METHOD AND APPARATUS, ELECTRONIC MEDICAL DEVICE, AND STORAGE MEDIUM" and filed with the China National Intellectual Property Administration on May 22, 2019, the entire contents of both of which are incorporated herein by reference.

FIELD OF THE TECHNOLOGY

The present disclosure relates to the field of computer technologies, and in particular, to a medical image processing method and apparatus, an electronic medical device, and a storage medium.

BACKGROUND OF THE DISCLOSURE

Breast cancer is one of common malignant diseases. In recent years, an incidence of female breast cancer is increasingly high. According to data statistics, there are up to 1.2 million newly increased breast cancer patients every year, and a morbidity rate the breast cancer ranks the first among the female malignant tumors. Breast imaging detection is an important means for breast cancer diagnosis, and currently common breast examination methods include: molybdenum target imaging, B ultrasonic detection, and nuclear magnetic resonance imaging. The molybdenum target imaging is the most common method, and therefore, medical diagnosis based on a molybdenum target breast image has a great medical significance.

SUMMARY

Embodiments of the present disclosure provide a medical image processing method and apparatus, an electronic medical device, and a storage medium, to improve the efficiency of recognizing a lesion category and lesion quadrant position information.

One aspect of the embodiments of the present disclosure provides a medical image processing method, performed by an electronic device, the method including: obtaining a biological tissue image including a biological tissue, recognizing, in the biological tissue image, a first region of a lesion object in the biological tissue; recognizing a lesion attribute matching the lesion object; dividing an image region of the biological tissue in the biological tissue image into a plurality of quadrant regions; obtaining target quadrant position information of a quadrant region in which the first region is located; and generating medical service data according to the target quadrant position information and the lesion attribute.

Another aspect of the embodiments of the present disclosure provides a medical image processing apparatus, including: obtain a biological tissue image including a biological tissue, recognize, in the biological tissue image, a first region of a lesion object in the biological tissue; recognize a lesion attribute matching the lesion object; divide an image region of the biological tissue in the biological tissue image into a plurality of quadrant regions, obtain target quadrant position information of a quadrant region in which the first region is located; and generate medical service data according to the target quadrant position information and the lesion attribute.

Another aspect of the embodiments of the present disclosure provides an electronic medical device, including a biological tissue image acquirer and a biological tissue image analyzer, the biological tissue image acquirer obtaining a biological tissue image including a biological tissue; the biological tissue image analyzer recognizing, in the biological tissue image, a first region of a lesion object in the biological tissue, and recognizing a lesion attribute matching the lesion object;

The biological tissue image analyzer dividing an image region of the biological tissue in the biological tissue image into a plurality of quadrant regions; and the biological tissue image analyzer obtaining target quadrant position information of a quadrant region in which the first region is located, and generating medical service data according to the target quadrant position information and the lesion attribute.

Another aspect of the embodiments of the present disclosure provides an electronic device, including a processor and a memory, the processor being connected to the memory, the memory being configured to store a program, and the processor being configured to invoke the program to perform: obtaining a biological tissue image including a biological tissue, recognizing, in the biological tissue image, a first region of a lesion object in the biological tissue; recognizing a lesion attribute matching the lesion object; dividing an image region of the biological tissue in the biological tissue image into a plurality of quadrant regions; obtaining target quadrant position information of a quadrant region in which the first region is located; and generating medical service data according to the target quadrant position information and the lesion attribute.

Another aspect of the embodiments of the present disclosure provides a non-transitory computer storage medium, storing a computer program, the computer program including program instructions, the program instructions, when executed by a processor, performing the method according to any embodiment of the present disclosure.

BRIEF DESCRIPTION OF THE DRAWINGS

To describe the technical solutions of the embodiments of the present disclosure more clearly, the following briefly introduces the accompanying drawings required for describing the embodiments. Apparently, the accompanying drawings in the following description show only some embodiments of the present disclosure, and a person of ordinary skill in the art may still derive other drawings from these accompanying drawings without creative efforts.

DESCRIPTION OF EMBODIMENTS

The technical solutions in embodiments of the present disclosure are clearly and completely described in the following with reference to the accompanying drawings in the embodiments of the present disclosure. Apparently, the described embodiments are merely some rather than all of the embodiments of the present disclosure. All other embodiments obtained by a person of ordinary skill in the art based on the embodiments of the present disclosure without creative efforts shall fall within the scope of the present disclosure.

In the related art, a molybdenum target breast image is mainly manually diagnosed by professional medical personnel. The professional medical personnel determine a lesion category and a lesion position for a lesion in the molybdenum target breast image based on experience, to generate a diagnosis result, and subsequently determines a treatment regimen based on the diagnosis result.

The manual diagnosis on a molybdenum target breast image by professional medical personnel needs to take a considerable amount of time, resulting in a low efficiency in diagnosing the molybdenum target breast image.

Figure 1:
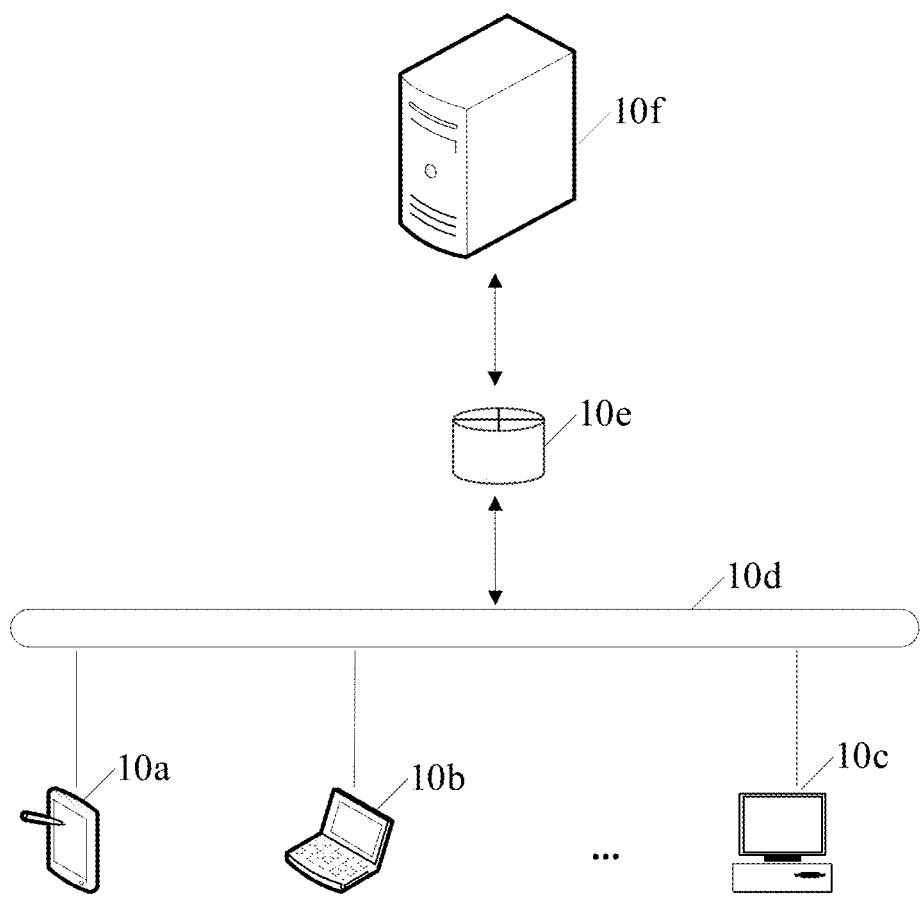
FIG. 1 is a system architecture diagram of medical image processing according to an embodiment of the present disclosure.

FIG. 1 is a system architecture diagram of medical image processing according to an embodiment of the present disclosure. A server 10f establishes a connection to a user terminal cluster by using a switch 10e and a communication bus 10d. The user terminal cluster may include: a user terminal 10a, a user terminal 10b, . . . , and a user terminal 10c.

The user terminal 10a is used as an example. When receiving a medical image including a lesion, the user terminal 10a transmits the medical image to the server 10f by using the switch 10e and the communication bus 10d. The server 10f may recognize a category to which the lesion pertains and quadrant position information of the lesion in the medical image, and generate medical service data according to a result obtained through recognition. The server 10f may transmit the medical service data to the user terminal 10a, and the user terminal 10a may subsequently display the medical service data on a screen.

Certainly, the user terminal 10a may alternatively recognize a category to which the lesion pertains and quadrant position information of the lesion in the medical image, and further generate medical service data. Similarly, the user terminal 10a may display the medical service data on a screen.

How the user terminal 10a recognizes the category to which the lesion pertains and the quadrant position information of the lesion in the medical image is used as an example below for detailed description.

The user terminal 10a, the user terminal 10b, the user terminal 10c, and the like shown in FIG. 1 may include a mobile phone, a tablet computer, a notebook computer, a palmtop computer, a mobile Internet device (MID), a wearable device (for example, a smart watch or a smart bracelet), and the like.

Figure 2A:
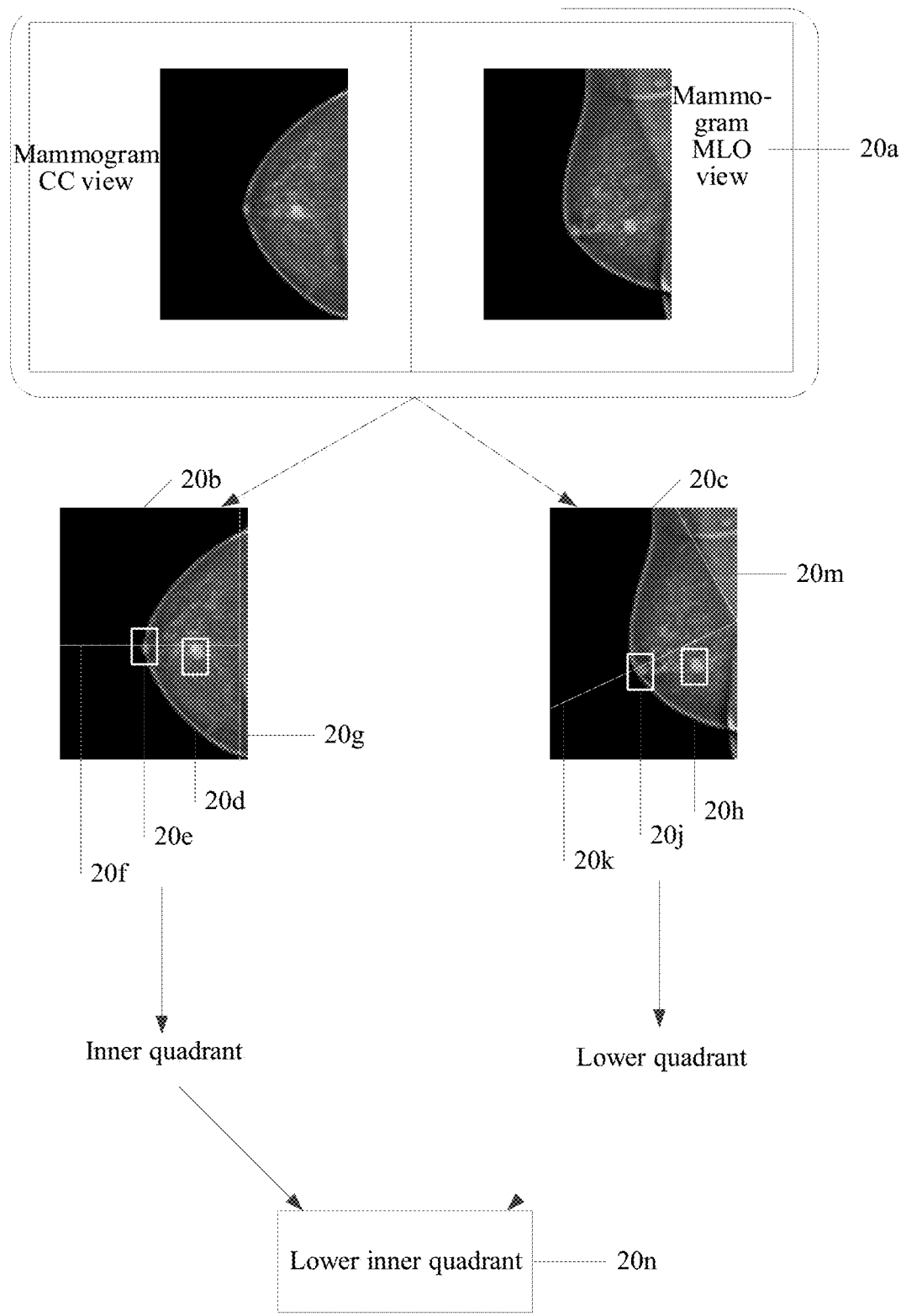
FIG. 2A and FIG. 2B are schematic diagrams of scenarios of medical image processing according to an embodiment of the present disclosure.
Figure 2B:
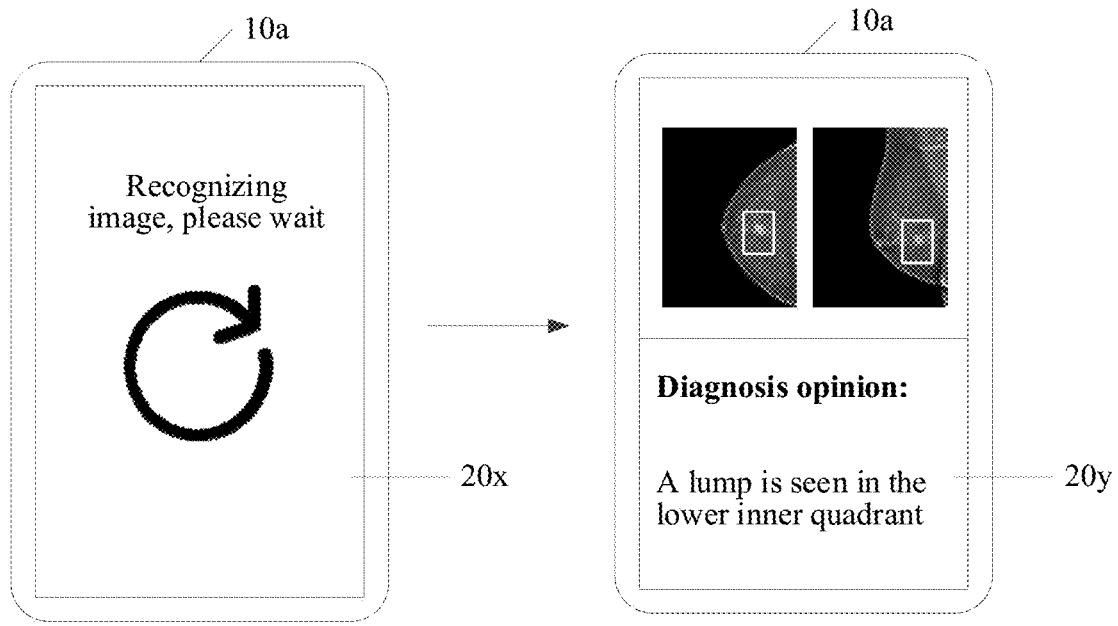

FIG. 2A to FIG. 2B are schematic diagrams of scenarios of medical image processing according to an embodiment of the present disclosure. As shown in an interface 20a in FIG. 2A, the user terminal 10a obtains a mammogram image at the same side of the same patient, and displays the obtained mammogram image on a screen. The mammogram image includes a mammogram image of craniocaudal (CC) view 20b and a mammogram image of mediolateral oblique (MLO) view 20c. The mammogram image of CC view is an image of a breast in a CC position, and the mammogram image of MLO view is an image of the breast in an MLO position. In some embodiments, the mammogram image may be obtained with molybdenum targets.

The user terminal 10a obtains a lump detection model and a calcification detection model. The lump detection model may identify a position region in which a lump lesion is located in an image. The calcification detection model may recognize a position region in which a calcification lesion is located in an image. A lump category and a calcification category are lesion categories.

For the lump detection model, the user terminal 10a may input the mammogram image of CC view 20b to the lump detection model, and the lump detection model may output a lesion region 20d of a lesion object, which is in the mammogram image of CC view 20b, in the mammogram image of CC view 20b, and may further determine a lesion category to which the lesion object in the mammogram image of CC view 20b pertains as the lump category.

The user terminal 10a may input the mammogram image of MLO view 20c to the lump detection model, and the lump detection model may alternatively output a lesion region 20h of a lesion object, which is in the mammogram image of MLO view 20c, in the mammogram image of MLO view 20c, and may further determine a lesion category to which the lesion object in the mammogram image of MLO view 20c pertains as the lump category.

For the calcification detection model, the user terminal 10a similarly inputs the mammogram image of CC view 20b to the calcification detection model, and no calcification lesion is detected in the mammogram image of CC view 20b by the calcification detection model. The user terminal 10a similarly inputs the mammogram image of MLO view 20c to the calcification detection model, and likewise no calcification lesion is detected in the mammogram image of MLO view 20c by the calcification detection model.

Therefore, for the mammogram image of CC view 20b and the mammogram image of MLO view 20c, there is merely the lump lesion. In addition, the lump lesion in the mammogram image of CC view 20b is located in the lesion region 20d, and the lump lesion in the mammogram image of MLO view 20c is located in the lesion region 20h.

The user terminal 10a obtains an image semantic segmentation model. The image semantic segmentation model may recognize a tissue category to which each pixel in an image pertains. The tissue category includes: a nipple category, a muscle category, and a background category.

The user terminal 10a inputs the mammogram image of CC view 20b to the image semantic segmentation model, and the model may determine a tissue category to which each pixel of the mammogram image of CC view 20b pertains. In the mammogram image of CC view 20b, the user terminal 10a combines pixels pertaining to the nipple category into a region 20e. The region 20e is a region in which a nipple is located. The user terminal 10a determines a breast edge line 20g in the mammogram image of CC view 20b, and uses a line 20f that is perpendicular to the breast edge line 20g and passes through the region 20e as a quadrant segmentation line 20f. In the mammogram image of CC view 20b, a part below the quadrant segmentation line 20f is an inner quadrant, and a part above the quadrant segmentation line 20f is an outer quadrant. In the mammogram image of CC view 20b, because the lesion region 20d is located in the inner quadrant (if most of the lesion region 20d is located in the inner quadrant, it is considered that the lesion region 20d is located in the inner quadrant), the user terminal 10a may determine that the lump lesion in the mammogram image of CC view 20b is located in the inner quadrant.

The user terminal 10a inputs the mammogram image of MLO view 20c to the image semantic segmentation model, and the model may determine a tissue category to which each pixel of the mammogram image of MLO view 20c pertains. In the mammogram image of MLO view 20c, the user terminal 10a combines pixels pertaining to the nipple category into a region 20j. The region 20j is a region in which a nipple is located. The user terminal 10a combines pixels pertaining to the muscle category into a muscle region, determines a region boundary 20m between the muscle region and a non-muscle region, and uses a line 20k that is perpendicular to the region boundary 20m and passes through the region 20j as a quadrant segmentation line 20k. In the mammogram image of MLO view 20c, a part below the quadrant segmentation line 20k is a lower quadrant, and a part above the quadrant segmentation line 20k is an upper quadrant. In the mammogram image of MLO view 20c, because the lesion region 20h is located in the lower quadrant, the user terminal 10a may determine that the lump lesion in the mammogram image of MLO view 20c is located in the lower quadrant.

The user terminal 10a combines the inner quadrant determined according to the mammogram image of CC view 20b and the lower quadrant determined according to the mammogram image of MLO view 20c into quadrant position information 20n, "lower inner quadrant".

The user terminal 10a may combine the quadrant position information 20n, "lower inner quadrant", and the lesion category "lump" that corresponds to both the mammogram image of CC view 20b and the mammogram image of MLO view 20c into a diagnosis opinion that "A lump is seen in the lower inner quadrant".

As shown in an interface 20x in FIG. 2B, the user terminal 10a may play a preset animation on the screen when recognizing the mammogram image of CC view 20b and the mammogram image of MLO view 20c. When detecting that recognition of the mammogram image of CC view 20b and the mammogram image of MLO view 20c is completed, as shown in an interface 20y, the user terminal stops playing the animation, and displays the generated diagnosis opinion on the screen. Further, the user terminal may further mark the lesion region recognized in the mammogram image of CC view 20b and the lesion region recognized in the mammogram image of MLO view 20c, by using rectangular boxes, in the corresponding mammogram image.

For specific processes of recognizing the lesion category to which the lesion object pertains, determining the lesion region of the lesion object in the image, determining the quadrant segmentation line, and determining the quadrant position information, refer to the following embodiments corresponding to FIG. 3 to FIG. 7B.

Figure 3:
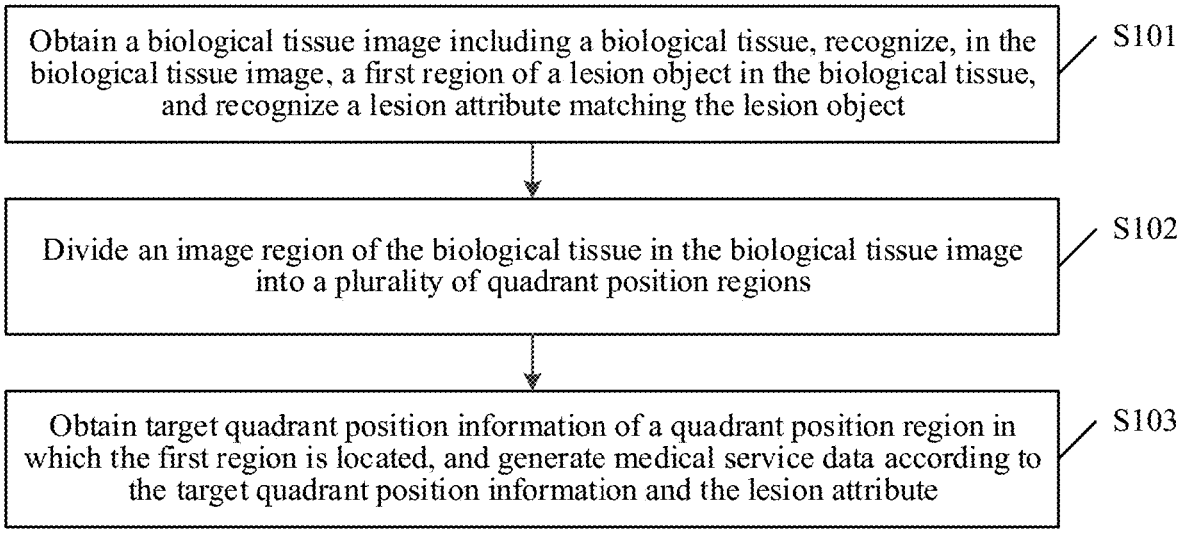
FIG. 3 is a schematic flowchart of a medical image processing method according to an embodiment of the present disclosure.

FIG. 3 is a schematic flowchart of a medical image processing method according to an embodiment of the present disclosure. As shown in FIG. 3, the medical image processing method may include the following steps:

Step S101. Obtain a biological tissue image including a biological tissue, recognize, in the biological tissue image, a first region of a lesion object in the biological tissue, and recognize a lesion attribute matching the lesion object.

Specifically, the terminal device (for example, the user terminal 10a in the foregoing embodiment corresponding to FIG. 2A) obtains the biological tissue image including the biological tissue (such as the mammogram image of CC view 20b and the mammogram image of MLO view 20c in the foregoing embodiment corresponding to FIG. 2A), and the biological tissue includes the lesion object. The biological tissue may be a breast, a liver, a kidney, or the like.

The terminal device recognizes a region of the lesion object in the biological tissue image as the first region (such as the lesion region 20d and the lesion region 20h in the foregoing embodiment corresponding to FIG. 2A), and the terminal device recognizes the lesion attribute corresponding to the lesion object.

For example, when the biological tissue is the breast, the lesion attribute may include: a lump, calcification, a distorted structure, and the like. When the biological tissue is the liver, the lesion attribute may include: a hemangioma, a liver abscess, a hepatic cyst, and the like. When the biological tissue is the kidney, the lesion attribute may include: a renal cyst, a kidney neoplasm, and the like.

The position region of the lesion object in the biological tissue image and the lesion attribute may be determined based on a plurality of lesion detection models (such as the lump detection model and the calcification detection model in the foregoing embodiment corresponding to FIG. 2A). One lesion detection model corresponds to one lesion attribute, and each lesion detection model may determine whether an attribute of a lesion object in a biological tissue image is the attribute corresponding to the model. If the attribute of the lesion object is the attribute corresponding to the model, a position region of the lesion object in the biological tissue image may be further determined.

For example, if there are two lesion detection models, the lesion attribute corresponding to a lesion detection model A is a lump, and the lesion attribute corresponding to a lesion detection model B is calcification. A biological tissue image is inputted to the lesion detection model A. If the lesion detection model A outputs a position region, it indicates that a lesion object is located in the position region, and the lesion attribute of the lesion object located in the position region is the lump. If the lesion detection model A does not output the position region, it indicates that the lump is not the lesion attribute of the lesion object. The same method may be used for the lesion detection model B for determining whether the lesion attribute of the lesion object is the calcification. If the lesion attribute is the calcification, the position region of the lesion object in the biological tissue image may be further determined.

There are two manners of recognizing the first region of the lesion object and the lesion attribute of the lesion object by the lesion detection model, and one of the two manners is first described in detail below. The terminal device obtains a plurality of sliding windows with fixed sizes. For example, the sizes of the sliding windows are 16×16, 16×32, 32×64, 64×16, and the like. Each sliding window slides on the biological tissue image, and is used for extracting a plurality of image blocks. A size of each image block is equal to the size of the sliding window, and a degree of overlap exists between the image blocks. In this way, it can be ensured that all regions in the biological tissue image can participate in subsequent recognition.

A lesion probability that the each image block pertains to the lesion attribute corresponding to the lesion detection model is recognized based on a classifier in the lesion detection model. If the recognized lesion probability of an image block is greater than a lesion probability threshold, it indicates that the image block includes a lesion object, a lesion attribute of the lesion object is determined as the lesion attribute corresponding to the lesion detection model, and a position region of the image block in the biological tissue image is further used as a candidate region of the lesion object. Certainly, if there is not an image block having a lesion probability greater than the lesion probability threshold, it indicates that the lesion attribute of the lesion object in the biological tissue image is not the lesion attribute corresponding to the lesion detection model. That is, no position region is detected in the lesion detection model.

The classifier in the lesion detection model is obtained through training by using image blocks including a sample lesion object and image blocks not including the sample lesion object, and a lesion attribute of the sample lesion object is equal to the lesion attribute corresponding to the lesion detection model. That is, the classifier is a binary classifier.

When there is only one candidate region, the candidate region may be directly used as the first region. When there are a plurality of candidate regions, although all the lesion probabilities corresponding to the candidate regions are greater than the probability threshold, overlap may exist between the candidate regions (that is, the plurality of candidate regions correspond to the same lesion object). Therefore, the first region of the lesion object in the biological tissue image may be subsequently determined from the plurality of candidate regions by using non-Maximum Suppression (NMS).

A specific process of the NMS is as follows: All the candidate regions are combined into a candidate region set, the terminal device may extract, from the candidate region set, a candidate region with a maximum lesion probability as a polling candidate region, determine an overlapping area between the polling candidate region and other candidate regions, then combine candidate regions with overlapping areas less than an area threshold into a new candidate region set, and next select, from the new candidate region set, a candidate region with the maximum lesion probability as the polling candidate region, and the process is repeated. When the candidate region set is empty, the polling candidate region is used as the first region of the lesion object in the biological tissue image.

Another manner of recognizing the first region of the lesion object and the lesion attribute of the lesion object by the lesion detection model is described in detail below. Convolution feature information may be obtained by performing a convolution operation on the biological tissue image based on a plurality of convolutional layers of the lesion detection model. The convolution feature information may be regarded as a plurality of feature maps.

Each convolutional layer corresponds to one or more convolution kernels (the kernel, may also be referred to as a filter or a receptive field). The convolution operation refers to a matrix multiply operation on the convolution kernels and subdata in different locations of input data. A quantity of channels of output data of each convolutional layer (which may be understood as a quantity of feature maps) is determined by a quantity of convolution kernels in the convolutional layer, and a height $H_{out}$ and a width $W_{out}$ of the output data (that is, the feature map) are jointly determined by a size of the input data, a size of the convolution kernel, a stride, and boundary padding. That is, $H_{out}=(H_{in}-H_{kernel}+2*padding)/stride+1$, and $W_{out}=(W_{in}-W_{kernel}+2*padding)/stride+1$. $H_{in}$, $H_{kernel}$ represent a height of the input data and a height of the convolution kernel respectively. $W_{in}$, $W_{kernel}$ represent a width of the input data and a width of the convolution kernel respectively.

With continued convolution, a data size of the convolution feature information (that is, a size of the feature map) is continuously reduced. For example, a size of the biological tissue image is H×W×1, a size of convolution feature information outputted after a first convolutional layer is passed through is $$\frac{H}{4}\times\frac{W}{4}\times 1,$$

and a size of convolution feature information outputted after a second convolutional layer passes through is $$\frac{H}{8}\times\frac{W}{8}\times 2.$$

The terminal device uses convolution feature information (or a feature map) obtained through last convolution as a convolutional heatmap (a size of the convolutional heatmap is m×n×2), and performs upsampling on the convolutional heatmap. That is, the terminal device enlarges the convolutional heatmap to the same size as the biological tissue image, to obtain a mask with a size of H×W×2, and may determine, according to the mask, a probability that the lesion attribute of the each pixel in the biological tissue image is the lesion attribute corresponding to the lesion detection model. The terminal device may use an image region formed by pixels with probabilities greater than the lesion probability threshold as the first region of the lesion object in the biological tissue image, and may determine that the lesion attribute of the lesion object in the first region is equal to the lesion attribute corresponding to the lesion detection model.

Certainly, if there is not a pixel having a probability greater than the lesion probability threshold, it indicates that the lesion attribute of the lesion object in the biological tissue image is not the lesion attribute corresponding to the lesion detection model. That is, no position region is detected in the lesion detection model.

When there are a plurality of lesion detection models, the lesion attribute of the lesion object in the biological tissue image and the first region may be separately determined in the foregoing manner.

The user terminal may mark the first region in the biological tissue image by using a rectangular box.

Step S102. Divide an image region of the biological tissue in the biological tissue image into a plurality of quadrant regions.

Specifically, the biological tissue includes a first tissue object. For example, when the biological tissue is a breast, the first tissue object may be a nipple. When the biological tissue is a liver, the first tissue object may be a liver capsule.

A region of the first tissue object in the biological tissue image is recognized as a second region (such as the region 20e and the region 20j in the foregoing embodiment corresponding to FIG. 2A). The second region may be determined based on an image semantic segmentation model. The image semantic segmentation model is used for recognizing an object attribute of the each pixel in the biological tissue image, and a working process of the image semantic segmentation model is similar to the second manner of determining the first region and the lesion attribute by the lesion detection model.

The terminal device determines quadrant segmentation lines (such as the quadrant segmentation line 20f and the quadrant segmentation line 20k in the foregoing embodiment corresponding to FIG. 2) in the biological tissue image according to the second region, uses the image region of the biological tissue in the biological tissue image as a tissue image region, and divides the tissue image region into a plurality of quadrant regions (such as the inner quadrant, the outer quadrant, the upper quadrant, and the lower quadrant in the foregoing embodiment corresponding to FIG. 2A) according to the quadrant segmentation lines.

Step S103. Obtain target quadrant position information of a quadrant region in which the first region is located, and generate medical service data according to the target quadrant position information and the lesion attribute.

Specifically, the terminal device obtains the quadrant position information (referred to as the target quadrant position information, for example, the quadrant position information 20n in the foregoing embodiment corresponding to FIG. 2A) of the quadrant region in which the first region is located. The terminal device generates the medical service data (for example, the diagnosis opinion in the foregoing embodiment corresponding to FIG. 2A) according to the target quadrant position information and the recognized lesion attribute.

Subsequently, the biological tissue image after the first region is marked by using the rectangular box and the medical service data may be displayed on the screen of the terminal device.

One embodiment of the present disclosure may provide a service in a manner of a software interface, in which single-side molybdenum target images in a plurality of projection positions, for example, a CC view and an MLO view, are inputted, and out of which medical service data is outputted.

Figure 4:
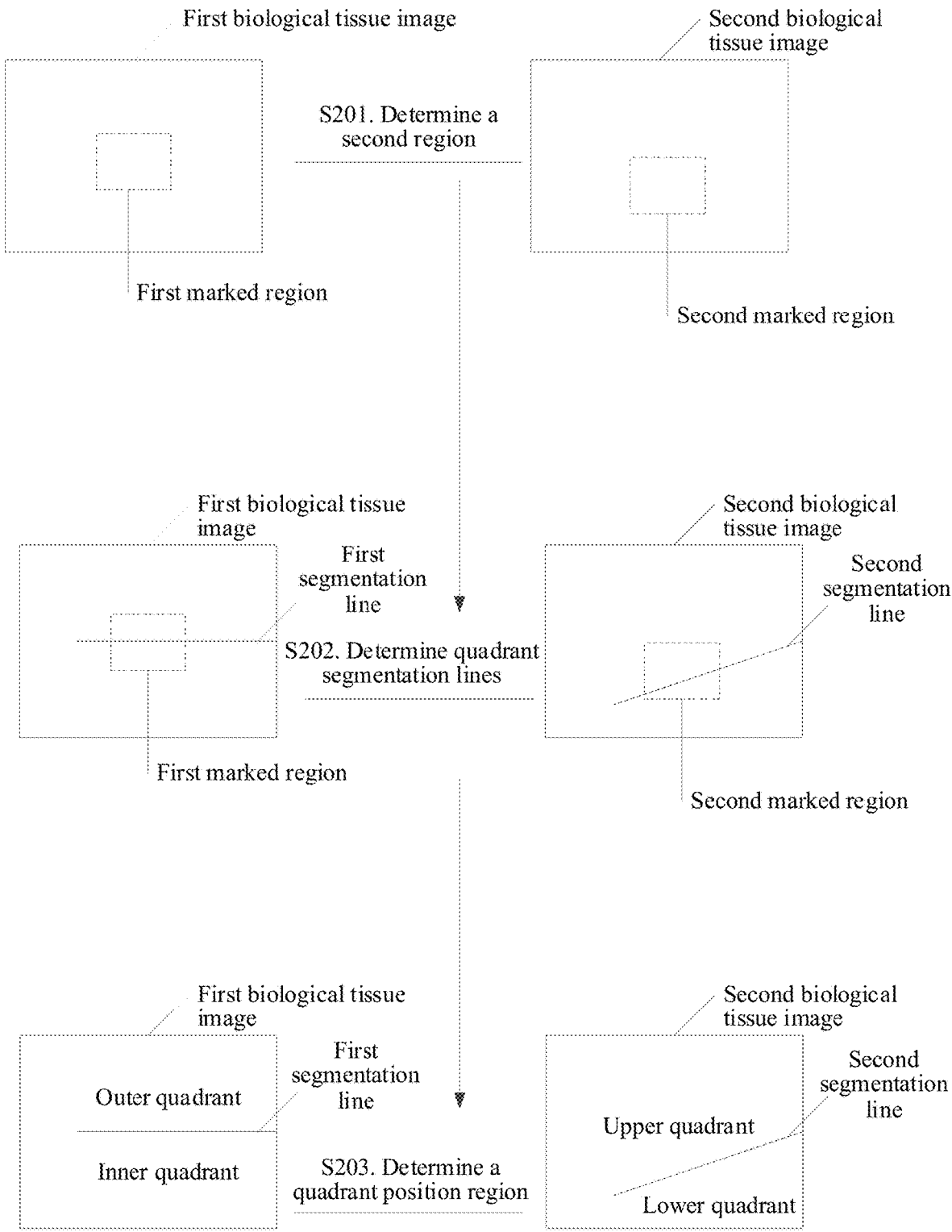
FIG. 4 is a schematic flowchart of determining a plurality of quadrant regions according to an embodiment of the present disclosure.

FIG. 4 is a schematic flowchart of determining a plurality of quadrant regions according to an embodiment of the present disclosure. The step of determining the plurality of quadrant regions includes step S201 to step S203, and step S201 to step S203 are a specific embodiment of step S102 in the foregoing embodiment corresponding to FIG. 3.

Step S201. Recognize a second region of the first tissue object in the biological tissue image.

Specifically, the biological tissue includes the first tissue object, and the biological tissue image includes a first biological tissue image (for example, the mammogram image of CC view 20b in the foregoing embodiment corresponding to FIG. 2A) and a second biological tissue image (for example, the mammogram image of MLO view 20c in the foregoing embodiment corresponding to FIG. 2A). The first biological tissue image and the second biological tissue image are images of the biological tissue in different views. For example, when the biological tissue is a breast, the first biological tissue image may be an image of the breast in a CC direction, and the second biological tissue image may be an image of the breast in an MLO direction.

Both the first biological tissue image and the second biological tissue image include the biological tissue and the first tissue object.

The terminal device obtains an image semantic segmentation model, inputs the first biological tissue image to the image semantic segmentation model, and may determine an image region, which is referred to as a first marked region (for example, the region 20e in the foregoing embodiment corresponding to FIG. 2A), of the first tissue object in the first biological tissue image based on the image semantic segmentation model. The terminal device inputs the second biological tissue image to the image semantic segmentation model, and may determine an image region, which is referred to as a second marked region (for example, the region 20j in the foregoing embodiment corresponding to FIG. 2A), of the first tissue object in the second biological tissue image based on the image semantic segmentation model.

The terminal device may determine the first marked region and the second marked region as the second region. That is, the second region includes the first marked region corresponding to the first biological tissue image and the second marked region corresponding to the second biological tissue image.

The image semantic segmentation model may be a fully convolutional network (FCN) model. A classification number of the model is set to 3, which represents a background, the first tissue object, and a second tissue object respectively. When the image semantic segmentation model is trained, weight initialization of the image semantic segmentation model may be performed by using a PASCAL VOC dataset and then using a public dataset Digital Database for Screening Mammography (DDSM, a digitalized database for breast X-ray screening), and finally transfer learning is performed by using domestic hospital data (a size of an input image may be 800×800 pixels, a batch processing size may be 8, a learning rate may be 0.00001, and a maximum quantity of iterations may be 10000), to finally obtain a fully convolutional segmentation network capable of extracting, from the biological tissue image, the region in which the first tissue object is located and a region in which the second tissue object is located.

The determining a first marked region in the first biological tissue image based on the image semantic segmentation model is described in detail below. The image semantic segmentation model includes a forward convolutional layer and a transposed convolutional layer. The forward convolutional layer is used for a forward convolution operation, and a size of a feature map can be reduced through the forward convolution operation. The transposed convolutional layer is used for a backward convolution operation, and the size of the feature map can be increased through the backward convolution operation.

The forward convolution operation is first performed on the first biological tissue image based on the forward convolutional layer, forward convolution feature information of the first biological tissue image is extracted, and the backward convolution operation is performed on the forward convolution feature information based on the transposed convolutional layer, to obtain a mask of H×W×3, where H,W represent a height and a width of the first biological tissue image respectively. The mask of H×W×3 includes: a background mask pertaining to a background category, a first tissue mask pertaining to a first tissue attribute, and a second tissue mask pertaining to a second tissue attribute, and sizes of the background mask, the first tissue mask, and the second tissue mask are all H×W. The first tissue attribute herein is used for identifying the first tissue object, and the second tissue attribute is used for identifying the second tissue object. When the biological tissue is a breast, the first tissue object may be a nipple, and the second tissue object may be a muscle.

A value of each unit mask in the mask represents a probability that the pixel corresponding to the first biological tissue image pertains to a corresponding attribute of the mask.

For each pixel in the first biological tissue image, an attribute corresponding to the mask with a maximum probability value, among the three masks, is used as an object attribute of the pixel, and it can be learned that the object attribute includes a background attribute, a first tissue attribute, and a second tissue attribute. Briefly, it can be determined according to the three masks that the each pixel pertains to the background attribute, the first tissue attribute, or the second tissue attribute.

The terminal device may use an image region formed by pixels pertaining to the first tissue object as the first marked region of the first tissue object in the first biological tissue image.

The same manner may be used for the second biological tissue image. That is, three masks are determined first, an object attribute of each pixel in the second biological tissue image is then determined according to the three masks, and similarly, the image region formed by the pixels pertaining to the first tissue object is used as the second marked region of the first tissue object in the second biological tissue image.

Step S202. Determine quadrant segmentation lines in the biological tissue image according to the second region.

Specifically, because the biological tissue image includes the first biological tissue image and the second biological tissue image, for the first biological tissue image, a first segmentation line (for example, the quadrant segmentation line 20$f$ in the foregoing embodiment corresponding to FIG. 2A) is determined in the first biological tissue image according to the first marked region. For the second biological tissue image, a second segmentation line (for example, the quadrant segmentation line 20$k$ in the foregoing embodiment corresponding to FIG. 2A) is determined in the second biological tissue image according to the second marked region. The first segmentation line and the second segmentation line are the quadrant segmentation lines.

How to determine the first segmentation line is described in detail below. The terminal device obtains an edge boundary (for example, the breast edge line 20$g$ in the foregoing embodiment corresponding to FIG. 2A) of the biological tissue in the first biological tissue image. When the biological tissue is a breast, the edge boundary may be a boundary at a rear edge of the breast. In the first biological tissue image, the terminal device uses a perpendicular line that is perpendicular to the edge boundary and passes through the first marked region as the first segmentation line.

How to determine the second segmentation line is described in detail below. The terminal device uses, according to the object attribute of the each pixel determined by the image semantic segmentation model, an image region formed by pixels pertaining to the second tissue attribute in the second biological tissue image as an object region, of the second tissue object in the second biological tissue image, in the second biological tissue image. For example, when the second tissue object is a muscle, the object region is a region of the muscle in the second biological tissue image.

For the second biological tissue image, the region in which the first tissue object (for example, a nipple) is located is the second marked region, the region in which the second tissue object (for example, a muscle) is located is the object region, and a remaining region is a background region. The terminal device determines a boundary between the object region and a non-object region as an object boundary (for example, the region boundary 20$m$ in the foregoing embodiment corresponding to FIG. 2A).

If the boundary between the object region and the non-object region is a curve, the curve is fitted to obtain a straight line, and the straight line is used as the object boundary. A sum of distances between points in the object boundary obtained through fitting and points in the curve before fitting is minimum. In the second biological tissue image, the terminal device uses a perpendicular line that is perpendicular to the object boundary and passes through the second marked region as the second segmentation line.

Step S203. Use an image region of the biological tissue in the biological tissue image as a tissue image region, and divide the tissue image region into a plurality of quadrant regions according to the quadrant segmentation lines.

Specifically, the first biological tissue image is an image of the biological tissue in a CC direction, and the second biological tissue image is an image of the biological tissue in an MLO direction. For example, when the biological tissue is a breast, the first biological tissue image may be a mammogram image of CC view, and the second biological tissue image may be a mammogram image of MLO view.

The terminal device uses an image region of the biological tissue in the first biological tissue image as a first tissue image region. In the first tissue image region, the terminal device uses a region located above the first segmentation line as an outer quadrant region, and uses a region below the first segmentation line as an inner quadrant region.

In other words, the inner quadrant region and the outer quadrant region may be determined according to the first biological tissue image.

The terminal device uses an image region of the biological tissue in the second biological tissue image as a second tissue image region. In the second tissue image region, the terminal device uses a region located above the second segmentation line as an upper quadrant region, and uses a region below the second segmentation line as a lower quadrant region.

In other words, the upper quadrant region and the lower quadrant region may be determined according to the second biological tissue image.

The terminal device may determine the inner quadrant region, the outer quadrant region, the upper quadrant region, and the lower quadrant region as the quadrant regions.

Figure 5:
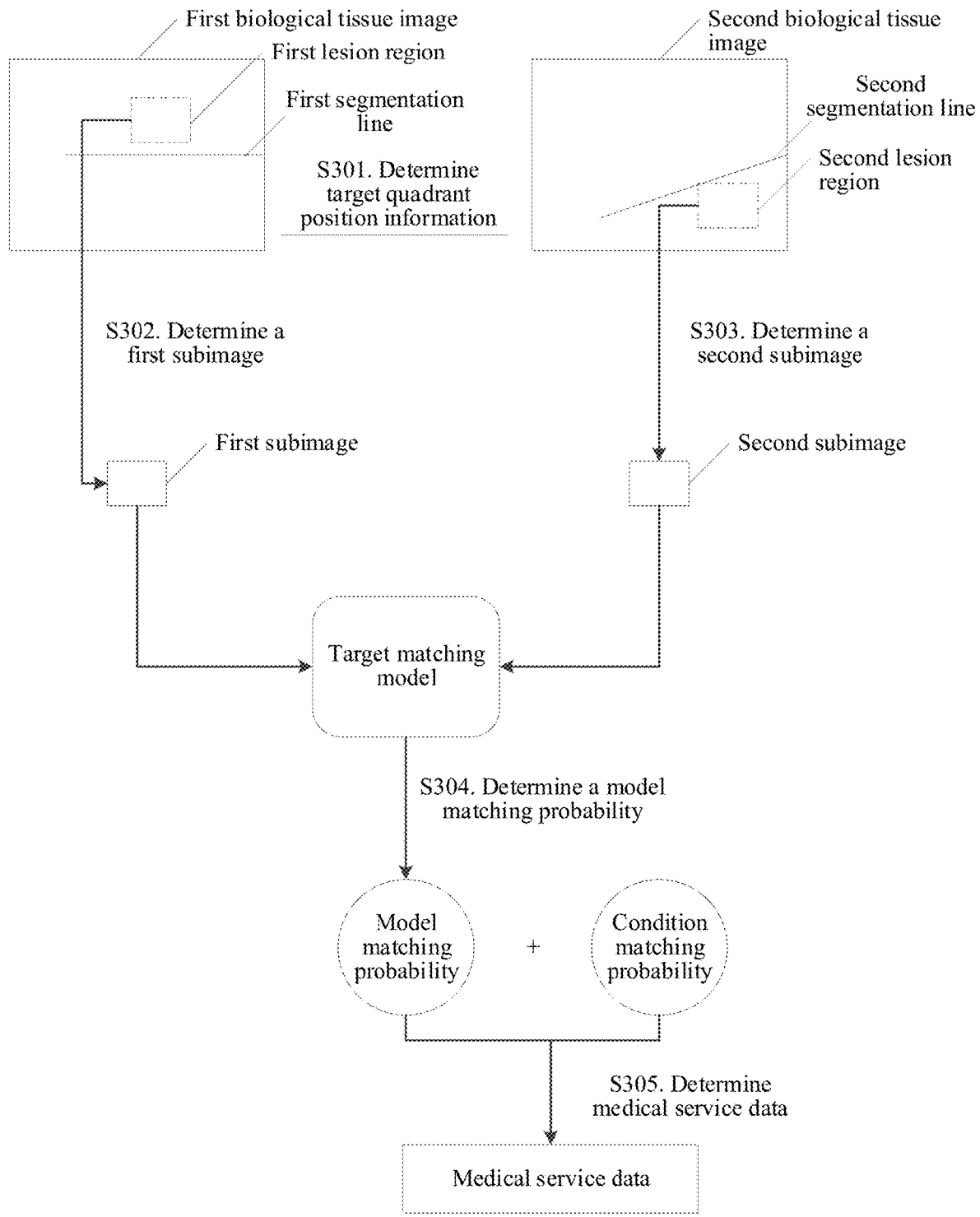
FIG. 5 is a schematic flowchart of generating medical service data according to an embodiment of the present disclosure.

FIG. 5 is a schematic flowchart of generating medical service data according to an embodiment of the present disclosure. The step of generating the medical service data includes step S301 to step S305, and step S301 to step S305 are a specific embodiment of step S103 in the foregoing embodiment corresponding to FIG. 3.

Step S301. Obtain target quadrant position information of a quadrant region in which the first region is located.

Specifically, because the biological tissue image includes the first biological tissue image and the second biological tissue image, the first region includes a first lesion region (for example, the lesion region 20*d* in the foregoing embodiment corresponding to FIG. 2A) of the lesion object in the first biological tissue image and a second lesion region (for example, the lesion region 20*h* in the foregoing embodiment corresponding to FIG. 2A) of the lesion object in the second biological tissue image.

When the first lesion region is located in the inner quadrant region in the first biological tissue image, and the second lesion region is located in the upper quadrant region in the second biological tissue image, the target quadrant position information is an upper inner quadrant.

When the first lesion region is located in the inner quadrant region in the first biological tissue image, and the second lesion region is located in the lower quadrant region in the second biological tissue image, the target quadrant position information is a lower inner quadrant.

When the first lesion region is located in the outer quadrant region in the first biological tissue image, and the second lesion region is located in the upper quadrant region in the second biological tissue image, the target quadrant position information is an upper outer quadrant.

When the first lesion region is located in the outer quadrant region in the first biological tissue image, and the second lesion region is located in the lower quadrant region in the second biological tissue image, the target quadrant position information is a lower outer quadrant.

Step S302. Extract a first subimage corresponding to the first lesion region from the first biological tissue image.

Specifically, the terminal device extracts a subimage in which the first lesion region is located from the first biological tissue image as the first subimage.

Step S303. Extract a second subimage corresponding to the second lesion region from the second biological tissue image.

Specifically, the terminal device extracts a subimage in which the second lesion region is located from the second biological tissue image as the second subimage.

Step S304. Obtain a target matching model, and recognize a model matching probability between the first subimage and the second subimage based on the target matching model.

Specifically, the terminal device obtains the target matching model. The target matching model may recognize whether the lesion objects included in the two images are the same lesion object. Because there may be a plurality of lesion objects in the biological tissue image, there are correspondingly a plurality of lesion objects in the first biological tissue image and a plurality of lesion objects in the second biological tissue image. The target matching model may be configured to recognize a matching probability between the lesion objects in the two images and determine a consistency between the lesion objects.

The terminal device inputs the first subimage to the target matching model, a convolutional layer and a pooling layer in the target matching model may extract first pooling feature information of the first subimage. The terminal device inputs the second subimage to the target matching model, the convolutional layer and the pooling layer in the target matching model may also extract second pooling feature information of the second subimage. The terminal device splices the first pooling feature information and the second pooling feature information into target pooling feature information in a column direction. A classifier in the target matching model recognizes a matching probability between the target pooling feature information and a matching category, and uses the matching probability as the model matching probability. The model matching probability may identify a probability that the lesion object in the first subimage and the lesion object in the second subimage are the same lesion object, and the matching probability is a real number between 0 and 1. The classifier in the target matching model is also a binary classifier, which not only may output the probability that the lesion object in the first subimage and the lesion object in the second subimage are the same lesion object, but also may output a probability that the lesion object in the first subimage and the lesion object in the second subimage are not the same lesion object.

Step S305. Obtain a condition matching probability between the first lesion region and the second lesion region, and combine the target quadrant position information and the lesion attribute into the medical service data when the model matching probability and the condition matching probability meet a lesion matching condition.

Specifically, the terminal device determines a size of the first lesion region in the first biological tissue image, which is referred to as a first size. The terminal device determines a size of the second lesion region in the second biological tissue image, which is referred to as a second size. When the first size is greater than the second size, the terminal device uses a value obtained by dividing the second size by the first size as a size matching probability. When the first size is less than the second size, the terminal device uses a value obtained by dividing the first size by the second size as a size matching probability, and it can be learned that the size matching probability is a real number between 0 and 1.

In the first biological tissue image, the terminal device determines a region distance (referred to as a first region distance) between the first lesion region and the image region (that is, the first marked region described above) corresponding to the first tissue object in the first biological tissue image. In second biological tissue image, the terminal device determines a region distance (referred to as a second region distance) between the second lesion region and the image region (that is, the second marked region) corresponding to the first tissue object in the second biological tissue image. When the first region distance is greater than the second region distance, the terminal device uses a value obtained by dividing the second region distance by the first region distance as a distance matching probability. When the first region distance is less than the second region distance, the terminal device uses a value obtained by dividing the first region distance by the second region distance as a distance matching probability, and the distance matching probability is also a real number between 0 and 1.

The terminal device uses the size matching probability and the distance matching probability as the condition matching probability.

If the size matching probability and the distance matching probability in the condition matching probability and the model matching probability are all greater than a preset probability threshold, it is determined that the model matching probability and the condition matching probability meet the lesion matching condition.

Alternatively, weight coefficients are separately set for the size matching probability and the distance matching probability in the model matching probability and the condition matching probability. If a sum of the model matching probability, the size matching probability, and the distance matching probability multiplied by the respective weight coefficients is greater than the preset probability threshold, it is determined that the model matching probability and the condition matching probability meet the lesion matching condition.

When the model matching probability and the condition matching probability meet the lesion matching condition, and there is only one lesion object in the biological tissue image, the terminal device may directly combine the determined target quadrant position information and lesion attribute into the medical service data.

When there are a plurality of lesion objects in the biological tissue image, correspondingly, there are a plurality of first subimages and a plurality of second subimages, and a quantity of the first subimages=a quantity of the second subimages=a quantity of the lesion objects. Correspondingly, the model matching probability includes a plurality of unit model matching probabilities, and each unit model matching probability is a matching probability between a first subimage and a second subimage determined by using the target matching model. The condition matching probability includes a plurality of unit condition matching probabilities, and each unit condition matching probability is the matching probability between a first subimage and a second subimage determined by using the size and the region distance. It can be learned that a quantity of the unit model matching probabilities=a quantity of the unit condition matching probabilities=a square of a quantity of the lesion objects.

A matching probability pair meeting the lesion matching condition is selected from the plurality of unit model matching probabilities and the plurality of unit condition matching probabilities as a target matching probability pair, each target matching probability pair including one unit model matching probability and one unit condition matching probability. It can be learned that the first subimage and the second subimage corresponding to each target matching pair correspond to the same lesion object. In this way, a paired lesion object (that is, the same lesion object) may be determined from the first biological tissue image and the second biological tissue image.

A lesion object of the target matching probability pair is used as a target lesion object when the unit model matching probability and the unit condition matching probability in the target matching probability pair meet the lesion matching condition. The terminal device combines target quadrant position information of the target lesion object and an object attribute of the target lesion object into the medical service data. An object attribute of the target lesion object determined in the first biological tissue image is the same as an object attribute of the target lesion object determined in the second biological tissue image.

For example, the biological tissue image includes two lesion objects, the first biological tissue image includes a lesion object 1 and a lesion object 2, and the second biological tissue image includes a lesion object 3 and a lesion object 4. Based on the lesion detection model A, it is determined that the lesion attributes of the lesion object 1, the lesion object 2, the lesion object 3, and the lesion object 4 are all lumps. The terminal device may obtain a first subimage 1 corresponding to the lesion object 1, a first subimage 2 corresponding to the lesion object 2, a second subimage 1 corresponding to the lesion object 3, and a second subimage 2 corresponding to the lesion object 4.

The terminal device determines, based on the target matching model, that a unit model matching probability between the first subimage 1 and the second subimage 1 is 0.9, a unit model matching probability between the first subimage 1 and the second subimage 2 is 0.2, a unit model matching probability between the first subimage 2 and the second subimage 1 is 0.1, and a unit model matching probability between the first subimage 2 and the second subimage 2 is 0.8.

The terminal device determines, according to the size of the lesion object and the region distance between the lesion object and the first tissue object, that a unit condition matching probability between the first subimage 1 and the second subimage 1 is 0.8, a unit condition matching probability between the first subimage 1 and the second subimage 2 is 0.1, a unit condition matching probability between the first subimage 2 and the second subimage 1 is 0.2, and a unit condition matching probability between the first subimage 2 and the second subimage 2 is 0.9.

From the four unit model matching probabilities and the four unit condition matching probabilities, the terminal device may determine that a unit model matching probability and a unit condition matching probability between the first subimage 1 and the second subimage 1 may be combined into the target matching pair, and that a unit model matching probability and a unit condition matching probability between the first subimage 2 and the second subimage 2 may be combined into the target matching pair.

Therefore, the lesion object 1 corresponding to the first subimage 1 and the lesion object 3 corresponding to the second subimage 1 are the same lesion object. The terminal device may use the lesion object 1 and the lesion object 3 as the target lesion object, and combine target quadrant position information and the lesion attribute "lump" that are determined according to the lesion object 1 and the lesion object 3 into the medical service data.

The lesion object 2 corresponding to the first subimage 2 and the lesion object 4 corresponding to the second subimage 2 are the same lesion object. The terminal device may use the lesion object 2 and the lesion object 4 as the target lesion object, and combine target quadrant position information and the lesion attribute "lump" that are determined according to the lesion object 2 and the lesion object 4 into the medical service data.

In an embodiment of the present disclosure, how to train the target matching model is described in detail below. The terminal device obtains a positive sample image and a negative sample image. The positive sample image includes a first positive sample image and a second positive sample image, and the first positive sample image and the second positive sample image correspond to the same lesion object. The negative sample image includes a first negative sample image and a second negative sample image, and the first negative sample image and the second negative sample image correspond to different lesion objects. The different lesion objects herein may mean that the lesion attributes are different, or may mean that the lesion attributes are the same, but the lesion objects are not the same.

The terminal device obtains an original matching model, where the original matching model is a class model obtained through training by using non-biological tissue images, for example, may be a classification model obtained through training by using landscape images, face images, or an ImageNet dataset. The terminal device selects, from model parameters included in the original matching model, model parameters of first n convolutional layers as target model parameters, for example, may select model parameters corresponding to first five convolutional layers in the original matching model as the target model parameters. The terminal device generates a sample matching model according to the target model parameters, the model parameters corresponding to the first n convolutional layers in the sample matching model being the target model parameters. The principle is an algorithm principle of transfer learning. That is, the sample matching model has some initial weights and is not randomly initialized, but is determined by another trained classification model. In this way, when the sample matching model is subsequently trained, only a small quantity of biological tissue images is required as the sample images to enable the sample matching model to converge.

After obtaining the sample matching model, the terminal device recognizes a positive sample prediction probability between the first positive sample image and the second positive sample image in the positive sample based on the sample matching model, and obtains a real matching probability between the first positive sample image and the second positive sample image as a positive sample probability, and it can be learned that the positive sample probability is 100%. The terminal device determines a positive sample error between the positive sample prediction probability and the positive sample probability, and adjusts the model parameters in the sample matching model through back propagation and based on the positive sample error.

Similarly, the terminal device recognizes a negative sample prediction probability between the first negative sample image and the second negative sample image in the negative sample based on the sample matching model, and obtains a real matching probability between the first negative sample image and the second negative sample image as a negative sample probability, and it can be learned that the negative sample probability is 0%. The terminal device determines a negative sample error between the negative sample prediction probability and the negative sample probability, and adjusts the model parameters in the sample matching model through back propagation and based on the negative sample error.

A gradient descent algorithm in the back propagation may use Adam, a batch processing size may be 128, an initial learning rate may be 0.001, and a maximum quantity of iterations may be 10000.

When a model parameter variation of the adjusted sample matching model is less than a variation threshold, or a quantity of times of adjustment is greater than a count threshold, or sample errors (including the positive sample error and the negative sample error) determined by the adjusted sample matching model are less than an error threshold, the terminal device may use the adjusted sample matching model as the target matching model.

Figure 6:
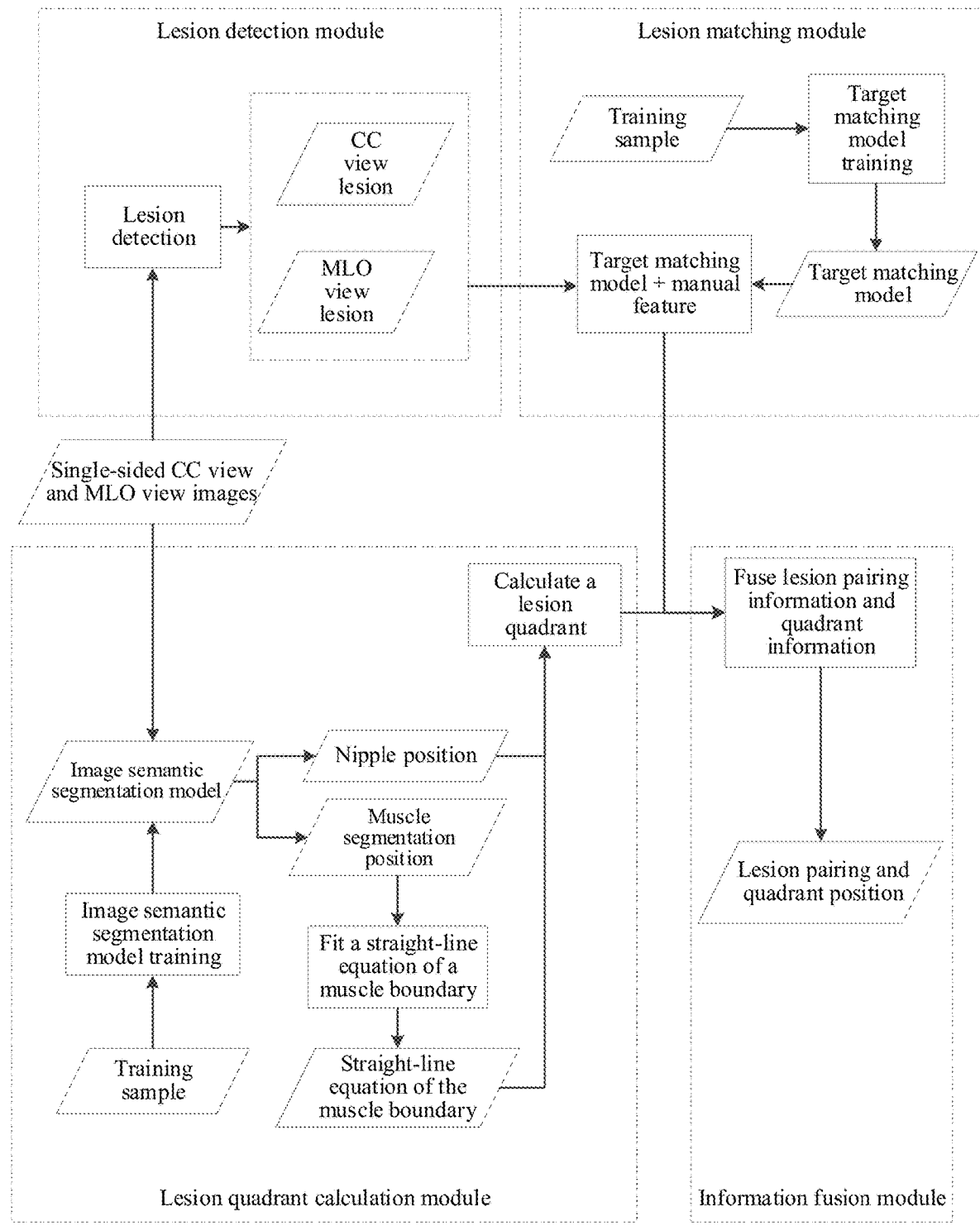
FIG. 6 is a schematic diagram of functional modules of medical image processing according to an embodiment of the present disclosure.

FIG. 6 is a schematic diagram of functional modules of medical image processing according to an embodiment of the present disclosure. A mammogram image of CC view (may also be referred as CC view image) and a mammogram image of MLO view (may also be referred as MLO view image) are used as an example below, and the CC view image and the MLO view image are images of the same breast in different views. The medical image processing includes four functional modules, namely, a lesion quadrant calculation module, a lesion detection module, a lesion matching module, and an information fusion module. After the terminal device obtains the CC view image and the MLO view image, the lesion detection module performs lesion detection on the two images, determines a first lesion region of a lesion object in the CC view image and recognizes a lesion attribute of the lesion object according to the CC view image. The first lesion region and the lesion attribute may be referred to as a CC view lesion. The lesion detection module determines a second lesion region of the lesion object in the MLO view image, and recognizes the lesion attribute of the lesion object according to the MLO view image. The second lesion region and the lesion attribute may be referred to as an MLO view lesion.

The lesion matching module obtains a target matching model, where the target matching model is obtained through training by using a plurality of positive sample images and a plurality of negative sample images. The lesion matching module determines a first subimage according to the first lesion region in the CC view lesion, and similarly determines a second subimage according to the second lesion region in the MLO view lesion. The lesion matching module inputs the first subimage and the second subimage to the target matching model, and the target matching model may recognize a model matching probability between the first subimage and the second subimage. The lesion matching module determines a condition matching probability according to sizes of the two lesion regions (that is, an image size of the first subimage and an image size of the second subimage) and a region distance between the two lesion regions and nipples in the respective biological tissue images, and may use the condition matching probability as a manual feature. The lesion matching module determines whether the model matching probability and the condition matching probability meet a lesion matching condition.

The lesion quadrant calculation module obtains an image semantic segmentation model. The image semantic segmentation model is obtained through training by using a plurality of sample images, each pixel in the sample image is marked, and a marking type includes a background attribute, a nipple attribute, and a muscle attribute. In other words, the image semantic segmentation model may recognize that each pixel in an image pertains to the background attribute, the nipple attribute, or the muscle attribute. The lesion quadrant calculation module inputs the CC view image to the image semantic segmentation model, and may determine a nipple position (the CC view image does not have muscle information, and therefore there is not a muscle region) in the CC view image based on the image semantic segmentation model, and the nipple position is the first marked region. The lesion quadrant calculation module inputs the MLO view image to the image semantic segmentation model, and may determine a nipple position (that is, the second marked region) and a muscle position (that is, the object region) in the MLO view image based on the image semantic segmentation model. For the CC view image, the lesion quadrant calculation module determines a first segmentation line according to the nipple position and a breast edge boundary, and determines, according to the first segmentation line, that the first lesion region is located in an inner quadrant or an outer quadrant. For the MLO view image, the lesion quadrant calculation module fits a straight-line equation of a muscle boundary according to the muscle position, to further determine the muscle boundary (that is, the object boundary), then determines a second segmentation line according to the nipple position and the muscle boundary, and determines that the second lesion region is located in an upper quadrant or a lower quadrant according to the second segmentation line.

When the model matching probability and the condition matching probability meet the lesion matching condition, the information fusion module fuses quadrant position information determined from the CC view image and quadrant position information determined from the MLO view image into target quadrant position information, and combines the target quadrant position information and the lesion attribute into medical service data. When there are a plurality of lesion objects, the information fusion module further needs to pair a plurality of first subimages and a plurality of second subimages, to separately determine target quadrant position information and a lesion attribute of a lesion object corresponding to each image pair.

Figure 7A:
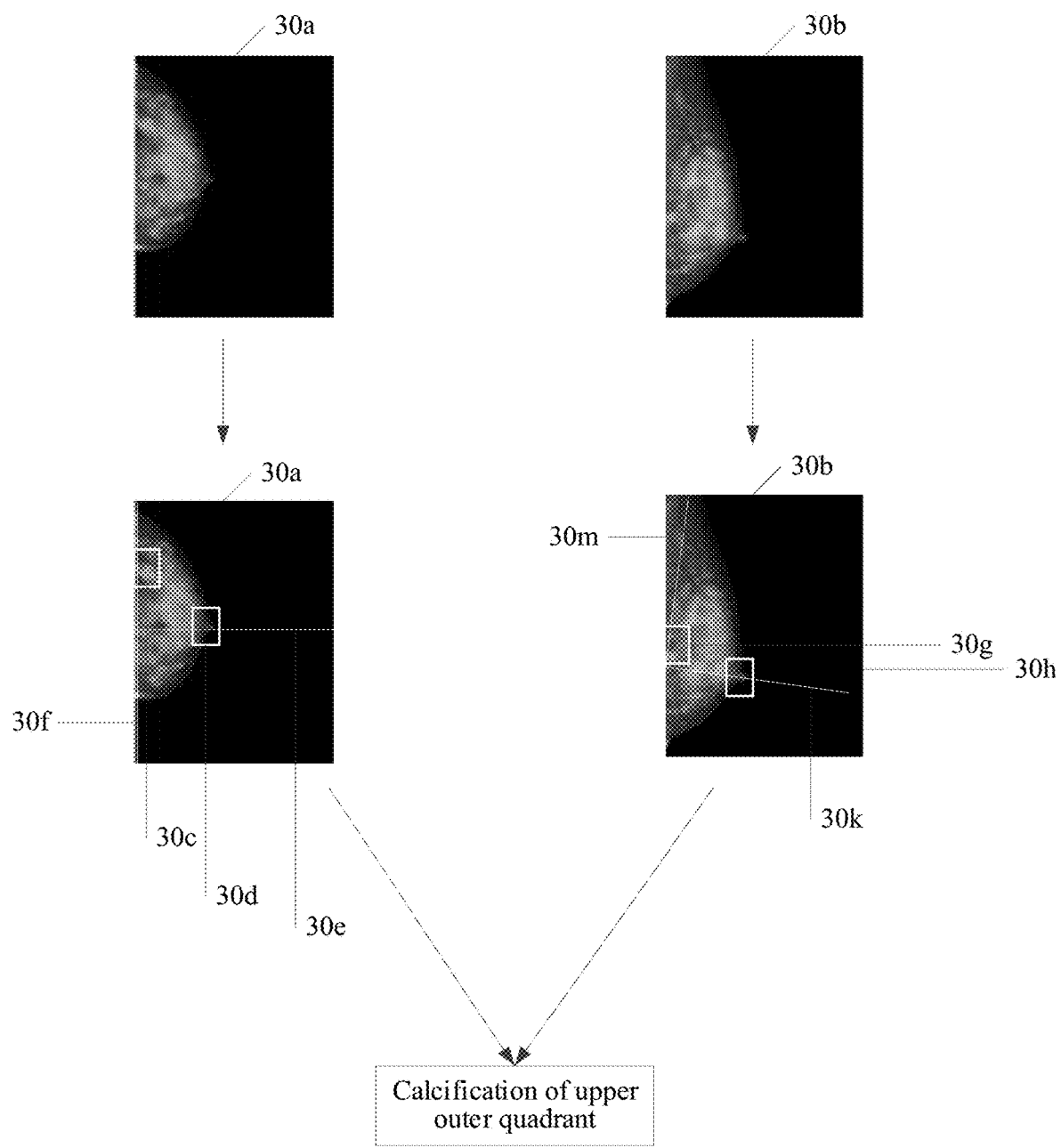
FIG. 7A is a schematic diagram of determining medical service data according to an embodiment of the present disclosure.

FIG. 7A is a schematic diagram of determining medical service data according to an embodiment of the present disclosure. An image 30a is a mammogram image of CC view, an image 30b is a mammogram image of MLO view, and the images 30a and 30b correspond to the same breast.

For the image 30a, a first lesion region 30c of a lesion object is determined first, and it is determined that a lesion attribute of the lesion object is calcification. A first marked region 30d in which a nipple (that is, a first tissue object) is located is recognized, and an edge boundary 30f of a breast is determined. The terminal device uses a perpendicular line 30e that is perpendicular to the edge boundary 30f and passes through the first marked region 30d as a first segmentation line 30e. Because the first lesion region 30c is located above the first segmentation line 30e, it is determined that the first lesion region 30c is located in an outer quadrant region.

For the image 30b, a second lesion region 30g of the lesion object is first determined, and it is determined that a lesion attribute of the lesion object is calcification. A second marked region 30h in which the nipple (that is, the first tissue object) is located is recognized. A position region in which a muscle (that is, the second tissue object) is located is determined based on an image semantic segmentation model, and an object boundary 30m is further determined. The terminal device uses a perpendicular line 30k that is perpendicular to the object boundary 30m and passes through the second marked region 30h as a second segmentation line 30k. Because the second lesion region 30g is located above the second segmentation line 30k, it is determined that the second lesion region 30g is located in an upper quadrant region.

Because the first lesion region 30c is located in the outer quadrant region, and the second lesion region 30g is located in the upper quadrant region, target quadrant position information is an upper outer quadrant. The target quadrant position information "upper outer quadrant" and the lesion attribute "calcification" are combined into the medical service data: calcification of the upper outer quadrant. Subsequently, the terminal device may display the medical service data, and at the same time, display, on a screen, the image 30a in which the first lesion region 30c is marked based on a rectangular box and the image 30b in which the second lesion region 30g is marked based on a rectangular box.

It can be learned from above that compared with manual diagnosis, a lesion category and lesion quadrant position information in a medical image are recognized in an automated manner, and the service data is further generated, so that time taken for determining the lesion category and the lesion quadrant position information can be reduced, and the efficiency and accuracy of determining the lesion category and the lesion quadrant position information can be improved.

Figure 7B:
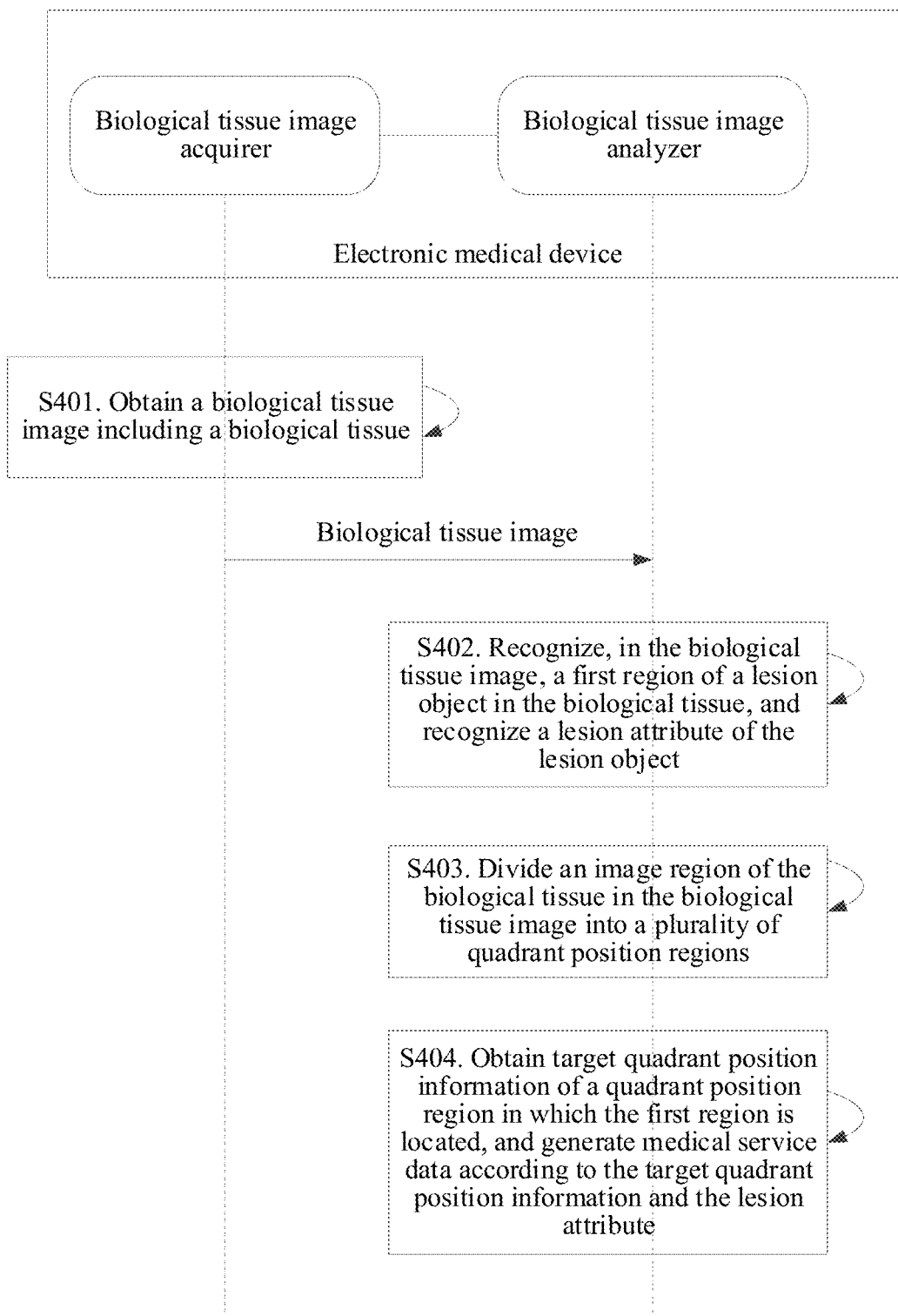
FIG. 7B is a schematic structural diagram of an electronic medical device according to an embodiment of the present disclosure.

FIG. 7B is a schematic structural diagram of an electronic medical device according to an embodiment of the present disclosure. The electronic medical device may be the terminal device in the embodiments corresponding to FIG. 3 and FIG. 7A. The electronic medical device includes a biological tissue image acquirer and a biological tissue image analyzer, and the electronic medical device may acquire medical images and analyze the medical images. A specific process includes the following steps:

Step S401. The biological tissue image acquirer obtains a biological tissue image including a biological tissue.

Specifically, the biological tissue image acquirer acquires the biological tissue image including the biological tissue. If the biological tissue is a breast, the biological tissue image acquirer may be a molybdenum target machine, and correspondingly, the biological tissue image is a mammogram image. If the biological tissue is a liver, the biological tissue image acquirer may be a B ultrasonic machine, and correspondingly, the biological tissue image is a liver B ultrasonic image. If the biological tissue is a brain, the biological tissue image acquirer may be a magnetic resonance imaging (MRI) instrument, and correspondingly, the biological tissue image is an MRI image.

Step S402. The biological tissue image analyzer recognizes, in the biological tissue image, a first region of a lesion object in the biological tissue, and recognizes a lesion attribute matching the lesion object.

Specifically, the biological tissue image analyzer recognizes a region of the lesion object, which is in the biological tissue, in the biological tissue image, which is referred to as the first region, and recognizes the lesion attribute of the lesion object.

The first region of the lesion object in the biological tissue image and the lesion attribute may be determined by the biological tissue image analyzer based on a plurality of lesion detection models. One lesion detection model corresponds to one lesion attribute, and each lesion detection model may determine whether an attribute of a lesion object in a biological tissue image is the attribute corresponding to the model. If the attribute of the lesion object is the attribute corresponding to the model, a position region of the lesion object in the biological tissue image may be further determined.

The biological tissue image analyzer determines, based on an NMS algorithm, the first region from the position region determined by the model. For a specific process of determining the first region and the lesion attribute of the lesion object by the biological tissue image analyzer, refer to step S101 in the foregoing embodiment corresponding to FIG. 3.

Step S403. The biological tissue image analyzer divides an image region of the biological tissue in the biological tissue image into a plurality of quadrant regions.

Specifically, the biological tissue includes a first tissue object. The biological tissue image analyzer recognizes a second region of the first tissue object in the biological tissue image. The biological tissue image analyzer determines quadrant segmentation lines in the biological tissue image according to the second region, and uses the image region of the biological tissue in the biological tissue image as a tissue image region. The biological tissue image analyzer divides the tissue image region into the plurality of quadrant regions according to the quadrant segmentation lines.

For a specific process of determining the plurality of quadrant regions by the biological tissue image analyzer, refer to step S201 to step S203 in the foregoing embodiment corresponding to FIG. 4.

Step S404. The biological tissue image analyzer obtains target quadrant position information of a quadrant region in which the first region is located, and generates medical service data according to the target quadrant position information and the lesion attribute.

Specifically, the biological tissue image analyzer obtains the quadrant position information (referred to as the target quadrant position information) of the quadrant region in which the first region is located. The biological tissue image analyzer generates the medical service data according to the target quadrant position information and the recognized lesion attribute, displays a biological tissue image after the first region is marked by a rectangular box on a screen of the electronic medical device, and displays the medical service data.

Figure 8:
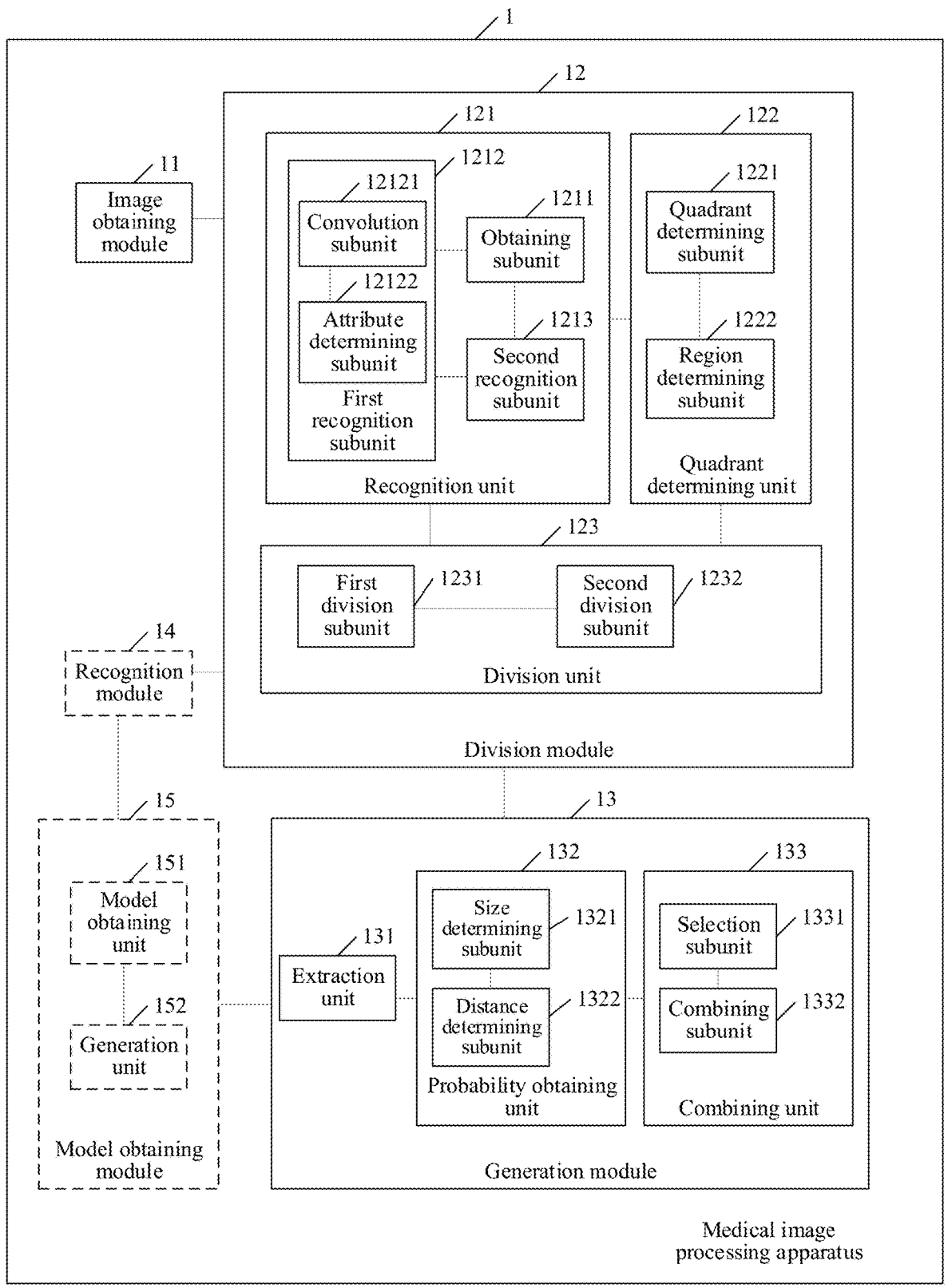
FIG. 8 is a schematic structural diagram of a medical image processing apparatus according to an embodiment of the present disclosure.

Further, FIG. 8 is a schematic structural diagram of a medical image processing apparatus according to an embodiment of the present disclosure. As shown in FIG. 8, the medical image processing apparatus 1 is applicable to the terminal device in the foregoing embodiments corresponding to FIG. 3 to FIG. 7A. The medical image processing apparatus 1 may include an image obtaining module 11, a division module 12, and a generation module 13.

The image obtaining module 11 is configured to obtain a biological tissue image including a biological tissue, recognize, in the biological tissue image, a first region of a lesion object in the biological tissue, and recognize a lesion attribute matching the lesion object.

The division module 12 is configured to divide an image region of the biological tissue in the biological tissue image into a plurality of quadrant regions.

The image obtaining module 11 is configured to obtain target quadrant position information of a quadrant region in which the first region is located.

The generation module 13 is configured to generate medical service data according to the target quadrant position information and the lesion attribute.

For specific functional implementations of the image obtaining module 11, the division module 12, and the generation module 13, refer to steps S101 to S103 in the foregoing embodiment corresponding to FIG. 3. Details are not described herein again.

Referring to FIG. 8, the biological tissue includes a first tissue object.

The division module 12 may include: a recognition unit 121, a quadrant determining unit 122, and a division unit 123.

The recognition unit 121 is configured to recognize a second region of the first tissue object in the biological tissue image.

The quadrant determining unit 122 is configured to determine quadrant segmentation lines in the biological tissue image according to the second region.

The division unit 123 is configured to use the image region of the biological tissue in the biological tissue image as a tissue image region, and divide the tissue image region into the plurality of quadrant regions according to the quadrant segmentation lines.

For specific functional implementations of the recognition unit 121, the quadrant determining unit 122, and the division unit 123, refer to step S201 to step S203 in the foregoing embodiment corresponding to FIG. 4. Details are not described herein again.

Referring to FIG. 8, the biological tissue image includes a first biological tissue image and a second biological tissue image, and the first biological tissue image and the second biological tissue image are images of the biological tissue in different views.

The recognition unit 121 may include: an obtaining subunit 1211, a first recognition subunit 1212, and a second recognition subunit 1213.

The obtaining subunit 1211 is configured to obtain an image semantic segmentation model.

The first recognition subunit 1212 is configured to determine a first marked region of the first tissue object in the first biological tissue image based on the image semantic segmentation model.

The second recognition subunit 1213 is configured to determine a second marked region of the first tissue object in the second biological tissue image based on the image semantic segmentation model.

The second recognition subunit 1213 is further configured to determine the first marked region and the second marked region as the second region.

For specific functional implementations of the obtaining subunit 1211, the first recognition subunit 1212, and the second recognition subunit 1213, refer to step S201 in the foregoing embodiment corresponding to FIG. 4. Details are not described herein again.

Referring to FIG. 8, the first recognition subunit 1212 may include a convolution subunit 12121 and an attribute determining subunit 12122.

The convolution subunit 12121 is configured to perform forward convolution and backward convolution on the first biological tissue image based on a forward convolutional layer and a transposed convolutional layer in the image semantic segmentation model, to obtain a convolutional feature map.

The attribute determining subunit 12122 is configured to determine an object attribute of each pixel in the first biological tissue image according to the convolutional feature map, the object attribute including a first tissue attribute.

The attribute determining subunit 12122 is further configured to use an image region formed by pixels pertaining to the first tissue object as the first marked region of the first tissue object in the first biological tissue image.

For specific functional implementations of the convolution subunit 12121 and the attribute determining subunit 12122, refer to step S201 in the foregoing embodiment corresponding to FIG. 4. Details are not described herein again.

Referring to FIG. 8, the quadrant segmentation lines include a first segmentation line corresponding to the first biological tissue image and a second segmentation line corresponding to the second biological tissue image, and the object attribute further includes a second tissue attribute.

The quadrant determining unit 122 may include a quadrant determining subunit 1221 and a region determining subunit 1222.

The quadrant determining subunit 1221 is configured to obtain an edge boundary of the biological tissue in the first biological tissue image, and determine the first segmentation line in the first biological tissue image according to the first marked region and the edge boundary.

The region determining subunit 1222 is configured to use an image region formed by pixels pertaining to the second tissue attribute as an object region, of a second tissue object in the second biological tissue image, in the second biological tissue image.

The region determining subunit 1222 is configured to determine an object boundary of the object region, and determine the second segmentation line in the second biological tissue image according to the second marked region and the object boundary.

For specific functional implementations of the quadrant determining subunit 1221 and the region determining subunit 1222, refer to step S202 in the foregoing embodiment corresponding to FIG. 4. Details are not described herein again.

Referring to FIG. 8, the first biological tissue image is an image of the biological tissue in a CC direction, and the second biological tissue image is an image of the biological tissue in an MLO direction.

The division unit 123 may include a first division subunit 1231 and a second division subunit 1232.

The first division subunit 1231 is configured to use an image region of the biological tissue in the first biological tissue image as a first tissue image region, and divide the first tissue image region into an inner quadrant region and an outer quadrant region in the first biological tissue image according to the first segmentation line.

The second division subunit 1232 is configured to use an image region of the biological tissue in the second biological tissue image as a second tissue image region, and divide the second tissue image region into an upper quadrant region and a lower quadrant region in the second biological tissue image according to the second segmentation line.

The second division subunit 1232 is further configured to determine the inner quadrant region, the outer quadrant region, the upper quadrant region, and the lower quadrant region as the quadrant regions.

For specific functional implementations of the first division subunit 1231 and the second division subunit 1232, refer to step S203 in the foregoing embodiment corresponding to FIG. 4. Details are not described herein again.

Referring to FIG. 8, the first region includes a first lesion region of the lesion object in a first biological tissue image and a second lesion region of the lesion object in a second biological tissue image, and the biological tissue image includes the first biological tissue image and the second biological tissue image.

The generation module 13 may include: an extraction unit 131, a probability obtaining unit 132, and a combining unit 133.

The extraction unit 131 is configured to extract a first subimage corresponding to the first lesion region from the first biological tissue image.

The extraction unit 131 is further configured to extract a second subimage corresponding to the second lesion region from the second biological tissue image.

The extraction unit 131 is further configured to obtain a target matching model, and recognize a model matching probability between the first subimage and the second subimage based on the target matching model.

The probability obtaining unit 132 is configured to obtain a condition matching probability between the first lesion region and the second lesion region.

The combining unit 133 is configured to combine the target quadrant position information and the lesion attribute into the medical service data when the model matching probability and the condition matching probability meet a lesion matching condition.

For specific functional implementations of the extraction unit 131, the probability obtaining unit 132, and the combining unit 133, refer to step S301 to step S305 in the foregoing embodiment corresponding to FIG. 5. Details are not described herein again.

Referring to FIG. 8, the probability obtaining unit 132 may include a size determining subunit 1321 and a distance determining subunit 1322.

The size determining subunit 1321 is configured to determine a first size of the first lesion region in the first biological tissue image, determine a second size of the second lesion region in the second biological tissue image, and generate a size matching probability according to the first size and the second size.

The distance determining subunit 1322 is configured to determine a first region distance between the first lesion region and an image region corresponding to a first tissue object in the first biological tissue image, and determine a second region distance between the second lesion region and an image region corresponding to the first tissue object in the second biological tissue image.

The distance determining subunit 1322 is further configured to generate a distance matching probability according to the first region distance and the second region distance.

The distance determining subunit 1322 is further configured to determine the size matching probability and the distance matching probability as the condition matching probability.

For specific functional implementations of the size determining subunit 1321 and the distance determining subunit 1322, refer to step S305 in the foregoing embodiment corresponding to FIG. 5. Details are not described herein again.

Referring to FIG. 8, there are a plurality of lesion objects in the biological tissue image, the model matching probability includes unit model matching probabilities between first subimages of the plurality of lesion objects and second subimages of the plurality of lesion objects, and the condition matching probability includes unit condition matching probabilities between first lesion regions of the plurality of lesion objects and second lesion regions of the plurality of lesion objects.

The combining unit 133 may include a selection subunit 1331 and a combining subunit 1332.

The selection subunit 1331 is configured to select a matching probability pair meeting the lesion matching condition from a plurality of unit model matching probabilities and a plurality of unit condition matching probabilities as a target matching probability pair, the target matching probability pair including one unit model matching probability and one unit condition matching probability.

The combining subunit 1332 is configured to use a lesion object of the target matching probability pair as a target lesion object when the unit model matching probability and the unit condition matching probability in the target matching probability pair meet the lesion matching condition, and combine target quadrant position information of the target lesion object and a lesion attribute of the target lesion object into the medical service data.

For specific functional implementations of the selection subunit 1331 and the combining subunit 1332, refer to step S305 in the foregoing embodiment corresponding to FIG. 5. Details are not described herein again.

Referring to FIG. 8, the medical image processing apparatus 1 may include: the image obtaining module 11, the division module 12, and the generation module 13, and may further include a recognition module 14 and a model obtaining module 15.

The recognition module 14 is configured to obtain a positive sample image and a negative sample image, the positive sample image including a first positive sample image and a second positive sample image, the first positive sample image and the second positive sample image being corresponding to the same lesion object; and the negative sample image including a first negative sample image and a second negative sample image, the first negative sample image and the second negative sample image being corresponding to different lesion objects.

The model obtaining module 15 is configured to obtain a sample matching model.

The recognition module 14 is further configured to recognize a positive sample prediction probability between the first positive sample image and the second positive sample image based on the sample matching model, obtain a positive sample probability between the first positive sample image and the second positive sample image, and determine a positive sample error between the positive sample prediction probability and the positive sample probability.

The recognition module 14 is further configured to recognize a negative sample prediction probability between the first negative sample image and the second negative sample image based on the sample matching model, obtain a negative sample probability between the first negative sample image and the second negative sample image, and determine a negative sample error between the negative sample prediction probability and the negative sample probability.

The recognition module 14 is further configured to adjust the sample matching model according to the positive sample error and the negative sample error.

The recognition module 14 is further configured to determine an adjusted sample matching model as the target matching model when the adjusted sample matching model meets a convergence condition.

For specific functional implementations of the recognition module 14 and the model obtaining module 15, refer to step S305 in the foregoing embodiment corresponding to FIG. 5. Details are not described herein again.

Referring to FIG. 8, the model obtaining module 15 may include a model obtaining unit 151 and a generation unit 152.

The model obtaining unit 151 is configured to obtain an original matching model, the original matching model being obtained through training according to a non-biological tissue image.

The generation unit 152 is configured to extract target model parameters from model parameters included in the original matching model, and generate the sample matching model based on transfer learning and the target model parameters.

For specific functional implementations of the model obtaining unit 151 and the generation unit 152, refer to step S305 in the foregoing embodiment corresponding to FIG. 5. Details are not described herein again.

The term unit (and other similar terms such as subunit, module, submodule, etc.) in this disclosure may refer to a software unit, a hardware unit, or a combination thereof. A software unit (e.g., computer program) may be developed using a computer programming language. A hardware unit may be implemented using processing circuitry and/or memory. Each unit can be implemented using one or more processors (or processors and memory). Likewise, a processor (or processors and memory) can be used to implement one or more units. Moreover, each unit can be part of an overall unit that includes the functionalities of the unit.

Figure 9:
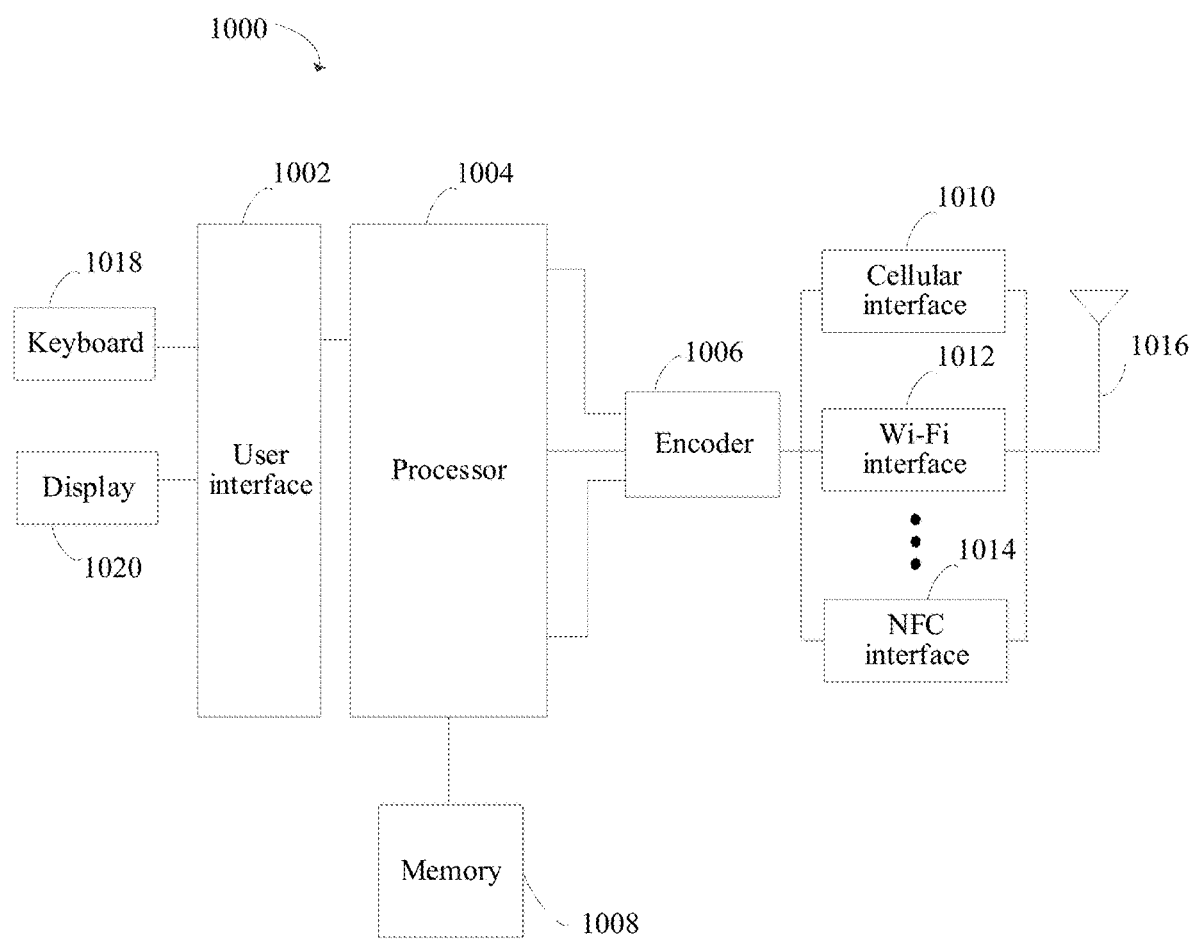
FIG. 9 is a schematic structural diagram of an electronic device according to an embodiment of the present disclosure.

Further, FIG. 9 is a schematic structural diagram of an electronic device according to an embodiment of the present disclosure. The terminal device in the foregoing embodiments corresponding to FIG. 3 to FIG. 7A may be an electronic device 1000. As shown in FIG. 9, the electronic device 1000 may include: a user interface 1002, a processor 1004, an encoder 1006, and a memory 1008. A signal receiver 1016 is configured to receive or transmit data through a cellular interface 1010, a Wi-Fi interface 1012, . . . , or an NFC interface 1014. The encoder 1006 encodes the received data into a computer-processed data format. The memory 1008 stores a computer program. The processor 1004 is configured to perform steps in any one of the method embodiments through the computer program. The memory 1008 may include a volatile memory (for example, a dynamic random access memory DRAM), and may further include a nonvolatile memory (for example, a one-time programmable read-only memory OTPROM). In some embodiments, the memory 1008 may further include memories remotely disposed relative to the processor 1004, and the remote memories may be connected to the electronic device 1000 through a network. The user interface 1002 may include a keyboard 1018 and a display 1020.

In the electronic device 1000 shown in FIG. 9, the processor 1004 may be configured to invoke the computer program stored in the memory 1008 to implement the following steps:

obtaining a biological tissue image including a biological tissue, recognizing, in the biological tissue image, a first region of a lesion object in the biological tissue, and recognizing a lesion attribute matching the lesion object;

dividing an image region of the biological tissue in the biological tissue image into a plurality of quadrant regions; and obtaining target quadrant position information of a quadrant region in which the first region is located, and generating medical service data according to the target quadrant position information and the lesion attribute.

The electronic device 1000 described in some embodiments of the present disclosure may perform the descriptions of the medical image processing method in the foregoing embodiments corresponding to FIG. 3 to FIG. 7B, or may perform the descriptions of the medical image processing apparatus 1 in the foregoing embodiment corresponding to FIG. 8. Details are not described herein again. In addition, beneficial effects achieved by using the same method are not described herein again.

In addition, an embodiment of the present disclosure further provides a computer storage medium. The computer storage medium stores a computer program executed by the medical image processing apparatus 1 mentioned above, and the computer program includes program instructions. When executing the program instructions, the processor can perform the descriptions of the medical image processing method in the foregoing embodiments corresponding to FIG. 3 to FIG. 7B. Therefore, details are not described herein again. In addition, beneficial effects achieved by using the same method are not described herein again. For technical details that are not disclosed in the computer storage medium embodiments of the present disclosure, refer to the descriptions of the method embodiments of the present disclosure.

A person of ordinary skill in the art may understand that some or all procedures in the method in the foregoing embodiments may be implemented by a computer program instructing related hardware. The program may be stored in a computer-readable storage medium, and when the program is executed, the procedures in the foregoing method embodiments may be implemented. The storage medium may be a magnetic disk, an optical disc, a read-only memory (ROM), a random access memory (RAM), or the like.

The foregoing disclosure is merely exemplary embodiments of the present disclosure, and certainly is not intended to limit the protection scope of the present disclosure. Therefore, equivalent variations made in accordance with the claims of the present disclosure fall within the scope of the present disclosure.

What is claimed is:

1. A medical image processing method, performed by an electronic device, the method comprising:
obtaining a biological tissue image comprising a biological tissue;
recognizing, in the biological tissue image, a first region of a lesion object in the biological tissue, the first region comprising a first lesion region and a second lesion region in the biological tissue image, the biological tissue image comprising a first biological tissue image and a second biological tissue image, and recognizing a lesion attribute matching the lesion object;

dividing an image region of the biological tissue in the biological tissue image into a plurality of quadrant regions;

obtaining target quadrant position information of a quadrant region in which the first region is located; and generating medical service data according to the target quadrant position information and the lesion attribute, comprising:

extracting a first subimage corresponding to the first lesion region from the first biological tissue image, extracting a second subimage corresponding to the second lesion region from the second biological tissue image;

obtaining a target matching model, and recognizing a model matching probability between the first subimage and the second subimage based on the target matching model; and obtaining a condition matching probability between the first lesion region and the second lesion region, and combining the target quadrant position information and the lesion attribute into the medical service data when the model matching probability and the condition matching probability meet a lesion matching condition.

2. The method according to claim 1, wherein the biological tissue comprises a first tissue object; and the dividing an image region of the biological tissue in the biological tissue image into a plurality of quadrant regions comprises:

recognizing a second region of the first tissue object in the biological tissue image;

determining quadrant segmentation lines in the biological tissue image according to the second region; and using the image region of the biological tissue in the biological tissue image as a tissue image region, and dividing the tissue image region into the plurality of quadrant regions according to the quadrant segmentation lines.

3. The method according to claim 2, wherein the the first biological tissue image and the second biological tissue image are images of the biological tissue in different views; and the recognizing a second region of the first tissue object in the biological tissue image comprises:

obtaining an image semantic segmentation model, and determining a first marked region of the first tissue object in the first biological tissue image based on the image semantic segmentation model;

determining a second marked region of the first tissue object in the second biological tissue image based on the image semantic segmentation model; and determining the first marked region and the second marked region as the second region.

4. The method according to claim 3, wherein the determining a first marked region of the first tissue object in the first biological tissue image based on the image semantic segmentation model comprises:

performing forward convolution and backward convolution on the first biological tissue image based on a forward convolutional layer and a transposed convolutional layer in the image semantic segmentation model, to obtain a convolutional feature map;

determining an object attribute of each pixel in the first biological tissue image according to the convolutional feature map, the object attribute comprising a first tissue attribute indicating whether a corresponding pixel pertains to the first tissue object; and using an image region formed by pixels pertaining to the first tissue object as the first marked region of the first tissue object in the first biological tissue image.

5. The method according to claim 4, wherein the quadrant segmentation lines comprise a first segmentation line corresponding to the first biological tissue image and a second segmentation line corresponding to the second biological tissue image, and the object attribute further comprises a second tissue attribute; and the determining quadrant segmentation lines in the biological tissue image according to the second region comprises:

obtaining an edge boundary of the biological tissue in the first biological tissue image, and determining the first segmentation line in the first biological tissue image according to the first marked region and the edge boundary;

using an image region formed by pixels pertaining to the second tissue attribute as an object region, of a second tissue object in the second biological tissue image, in the second biological tissue image; and determining an object boundary of the object region, and determining the second segmentation line in the second biological tissue image according to the second marked region and the object boundary.

6. The method according to claim 5, wherein the first biological tissue image is an image of the biological tissue in a craniocaudal view, and the second biological tissue image is an image of the biological tissue in a mediolateral oblique view; and the using the image region of the biological tissue in the biological tissue image as a tissue image region, and dividing the tissue image region into the plurality of quadrant regions according to the quadrant segmentation lines comprises:

using an image region of the biological tissue in the first biological tissue image as a first tissue image region, and dividing the first tissue image region into an inner quadrant region and an outer quadrant region in the first biological tissue image according to the first segmentation line;

using an image region of the biological tissue in the second biological tissue image as a second tissue image region, and dividing the second tissue image region into an upper quadrant region and a lower quadrant region in the second biological tissue image according to the second segmentation line; and determining the inner quadrant region, the outer quadrant region, the upper quadrant region, and the lower quadrant region as the quadrant regions.

7. The method according to claim 1, wherein the obtaining a condition matching probability between the first lesion region and the second lesion region comprises:

determining a first size of the first lesion region in the first biological tissue image, determining a second size of the second lesion region in the second biological tissue image, and generating a size matching probability according to the first size and the second size;

determining a first region distance between the first lesion region and an image region corresponding to a first tissue object in the first biological tissue image, and determining a second region distance between the second lesion region and an image region corresponding to the first tissue object in the second biological tissue image;
generating a distance matching probability according to the first region distance and the second region distance; and
determining the size matching probability and the distance matching probability as the condition matching probability.

8. The method according to claim 1, wherein there are a plurality of lesion objects in the biological tissue image, the model matching probability comprises unit model matching probabilities between first subimages of the plurality of lesion objects and second subimages of the plurality of lesion objects, and the condition matching probability comprises unit condition matching probabilities between first lesion regions of the plurality of lesion objects and second lesion regions of the plurality of lesion objects; and
the combining the target quadrant position information and the lesion attribute into the medical service data when the model matching probability and the condition matching probability meet a lesion matching condition comprises:
selecting a matching probability pair meeting the lesion matching condition from the plurality of unit model matching probabilities and the plurality of unit condition matching probabilities as a target matching probability pair, the target matching probability pair comprising one unit model matching probability and one unit condition matching probability; and
using a lesion object of the target matching probability pair as a target lesion object when the unit model matching probability and the unit condition matching probability in the target matching probability pair meet the lesion matching condition, and combining target quadrant position information of the target lesion object and a lesion attribute of the target lesion object into the medical service data.

9. The method according to claim 1, further comprising:
obtaining a positive sample image and a negative sample image, the positive sample image comprising a first positive sample image and a second positive sample image, the first positive sample image and the second positive sample image being corresponding to the same lesion object; and the negative sample image comprising a first negative sample image and a second negative sample image, the first negative sample image and the second negative sample image being corresponding to different lesion objects;
obtaining a sample matching model, recognizing a positive sample prediction probability between the first positive sample image and the second positive sample image based on the sample matching model, obtaining a positive sample probability between the first positive sample image and the second positive sample image, and determining a positive sample error between the positive sample prediction probability and the positive sample probability;
recognizing a negative sample prediction probability between the first negative sample image and the second negative sample image based on the sample matching model, obtaining a negative sample probability between the first negative sample image and the second negative sample image, and determining a negative sample error between the negative sample prediction probability and the negative sample probability;
adjusting the sample matching model according to the positive sample error and the negative sample error; and
determining an adjusted sample matching model as the target matching model when the adjusted sample matching model meets a convergence condition.

10. The method according to claim 9, wherein the obtaining a sample matching model comprises:
obtaining an original matching model, the original matching model being obtained through training according to a non-biological tissue image; and
extracting target model parameters from model parameters comprised in the original matching model, and generating the sample matching model based on transfer learning and the target model parameters.

11. A medical image processing apparatus, comprising: a processor and a memory, the processor being connected to the memory, the memory being configured to store a computer program, and the processor being configured to invoke the computer program to:
obtaining a biological tissue image comprising a biological tissue;
recognizing, the first region comprising a first lesion region and a second lesion region in the biological tissue image, the biological tissue image comprising a first biological tissue image and a second biological tissue image, in the biological tissue image, a first region of a lesion object in the biological tissue, and recognize a lesion attribute matching the lesion object;
dividing an image region of the biological tissue in the biological tissue image into a plurality of quadrant regions,
obtaining target quadrant position information of a quadrant region in which the first region is located; and
generating medical service data according to the target quadrant position information and the lesion attribute, comprising:
extracting a first subimage corresponding to the first lesion region from the first biological tissue image, extracting a second subimage corresponding to the second lesion region from the second biological tissue image;
obtaining a target matching model, and recognizing a model matching probability between the first subimage and the second subimage based on the target matching model; and
obtaining a condition matching probability between the first lesion region and the second lesion region, and combining the target quadrant position information and the lesion attribute into the medical service data when the model matching probability and the condition matching probability meet a lesion matching condition.

12. The apparatus according to claim 11, wherein the biological tissue comprises a first tissue object; and
the dividing an image region of the biological tissue in the biological tissue image into a plurality of quadrant regions comprises:
recognizing a second region of the first tissue object in the biological tissue image;
determining quadrant segmentation lines in the biological tissue image according to the second region; and
using the image region of the biological tissue in the biological tissue image as a tissue image region, and dividing the tissue image region into the plurality of quadrant regions according to the quadrant segmentation lines.

13. The apparatus according to claim 12, wherein the biological tissue image comprises a first biological tissue image and a second biological tissue image, and the first biological tissue image and the second biological tissue image are images of the biological tissue in different views; and the recognizing a second region of the first tissue object in the biological tissue image comprises:
obtaining an image semantic segmentation model, and determining a first marked region of the first tissue object in the first biological tissue image based on the image semantic segmentation model;
determining a second marked region of the first tissue object in the second biological tissue image based on the image semantic segmentation model; and
determining the first marked region and the second marked region as the second region.

14. The apparatus according to claim 13, wherein the determining a first marked region of the first tissue object in the first biological tissue image based on the image semantic segmentation model comprises:

performing forward convolution and backward convolution on the first biological tissue image based on a forward convolutional layer and a transposed convolutional layer in the image semantic segmentation model, to obtain a convolutional feature map;
determining an object attribute of each pixel in the first biological tissue image according to the convolutional feature map, the object attribute comprising a first tissue attribute indicating whether a corresponding pixel pertains to the first tissue object; and
using an image region formed by pixels pertaining to the first tissue object as the first marked region of the first tissue object in the first biological tissue image.

15. The apparatus according to claim 14, wherein the quadrant segmentation lines comprise a first segmentation line corresponding to the first biological tissue image and a second segmentation line corresponding to the second biological tissue image, and the object attribute further comprises a second tissue attribute; and the determining quadrant segmentation lines in the biological tissue image according to the second region comprises:
obtaining an edge boundary of the biological tissue in the first biological tissue image, and determining the first segmentation line in the first biological tissue image according to the first marked region and the edge boundary;
using an image region formed by pixels pertaining to the second tissue attribute as an object region, of a second tissue object in the second biological tissue image, in the second biological tissue image; and
determining an object boundary of the object region, and determining the second segmentation line in the second biological tissue image according to the second marked region and the object boundary.

16. The apparatus according to claim 15, wherein the first biological tissue image is an image of the biological tissue in a craniocaudal view, and the second biological tissue image is an image of the biological tissue in a mediolateral oblique view; and the using the image region of the biological tissue in the biological tissue image as a tissue image region, and dividing the tissue image region into the plurality of quadrant regions according to the quadrant segmentation lines comprises:

using an image region of the biological tissue in the first biological tissue image as a first tissue image region, and dividing the first tissue image region into an inner quadrant region and an outer quadrant region in the first biological tissue image according to the first segmentation line;
using an image region of the biological tissue in the second biological tissue image as a second tissue image region, and dividing the second tissue image region into an upper quadrant region and a lower quadrant region in the second biological tissue image according to the second segmentation line; and
determining the inner quadrant region, the outer quadrant region, the upper quadrant region, and the lower quadrant region as the quadrant regions.

17. The apparatus according to claim 11, wherein the obtaining a condition matching probability between the first lesion region and the second lesion region comprises:

determining a first size of the first lesion region in the first biological tissue image, determining a second size of the second lesion region in the second biological tissue image, and generating a size matching probability according to the first size and the second size;
determining a first region distance between the first lesion region and an image region corresponding to a first tissue object in the first biological tissue image, and determining a second region distance between the second lesion region and an image region corresponding to the first tissue object in the second biological tissue image;
generating a distance matching probability according to the first region distance and the second region distance; and
determining the size matching probability and the distance matching probability as the condition matching probability.

18. A non-transitory computer storage medium, storing a computer program, the computer program comprising program instructions, the program instructions, when executed by a processor, performing:

obtaining a biological tissue image comprising a biological tissue;
recognizing, the first region comprising a first lesion region and a second lesion region in the biological tissue image, the biological tissue image comprising a first biological tissue image and a second biological tissue image, in the biological tissue image, a first region of a lesion object in the biological tissue, and recognizing a lesion attribute matching the lesion object;
dividing an image region of the biological tissue in the biological tissue image into a plurality of quadrant regions;
obtaining target quadrant position information of a quadrant region in which the first region is located; and
generating medical service data according to the target quadrant position information and the lesion attribute, comprising:
extracting a first subimage corresponding to the first lesion region from the first biological tissue image, extracting a second subimage corresponding to the second lesion region from the second biological tissue image;
obtaining a target matching model, and recognizing a model matching probability between the first subimage and the second subimage based on the target matching model; and obtaining a condition matching probability between the first lesion region and the second lesion region, and combining the target quadrant position information and the lesion attribute into the medical service data when the model matching probability and the condition matching probability meet a lesion matching condition.

* * * * *